United States Patent [19]

Ribi

[11] Patent Number: 5,622,872
[45] Date of Patent: Apr. 22, 1997

[54] ANALYTE DETECTION THROUGH OBSERVED OPTICAL MODULATION OF POLYMERIZED LIPID LAYERS

[75] Inventor: Hans O. Ribi, Hillsborough, Calif.

[73] Assignee: Biocircuits Corporation, Sunnyvale, Calif.

[21] Appl. No.: 439,413

[22] Filed: May 11, 1995

Related U.S. Application Data

[60] Continuation of Ser. No. 149,075, Nov. 9, 1993, abandoned, which is a division of Ser. No. 893,563, Jul. 3, 1992, abandoned, which is a continuation of Ser. No. 453,784, Dec. 20, 1989, abandoned, which is a continuation-in-part of Ser. No. 366,651, Jun. 15, 1989, Pat. No. 5,156,810.

[51] Int. Cl.$^6$ ............................................. G01N 33/53
[52] U.S. Cl. .................... 436/518; 435/7.1; 435/7.5; 435/288.7; 436/532; 204/403; 422/82.08; 422/82.09
[58] Field of Search ....................... 435/4, 7.1, 14, 435/291, 288, 808, 817, 7.5, 288.7; 427/2.11; 436/518, 524, 528, 529, 531, 71, 149, 150, 532; 204/403; 356/352; 422/57–58, 82.06–82.09, 82.11

[56] References Cited

U.S. PATENT DOCUMENTS

| | | | |
|---|---|---|---|
| H201 | 1/1987 | Yager | 422/82.02 |
| 4,488,133 | 12/1984 | McClellan et al. | 335/16 |
| 4,591,550 | 5/1986 | Hafeman et al. | 435/4 |
| 4,859,538 | 8/1989 | Ribi | 428/474.4 |
| 5,087,952 | 2/1992 | Ribi | 357/25 |
| 5,156,810 | 10/1992 | Ribi | 422/82.01 |
| 5,268,305 | 12/1993 | Ribi et al. | 436/501 |
| 5,415,999 | 5/1995 | Saul et al. | 435/7.9 |
| 5,427,915 | 6/1995 | Ribi et al. | 435/7.92 |
| 5,491,097 | 2/1996 | Ribi et al. | 436/518 |

OTHER PUBLICATIONS

Chemical Abstract 100:218087.
Chemical Abstract 114(21): 203109.
Chemical Abstract 114(25: 243888.
Chemical Abstract 114(25): 243889.
Chemical Abstract 114(25): 243890.
M. Thompson et al, "The Structure and Electrochemical Properties of a Polymer–Supported Lipid Biosensor," Anal. Chim. Acta. 117: 133–145. (1980).
D. Charych et al., "Direct Colorimetric Detection of a Receptor–Legand Interaction by a Polymerized Bilayer Assembly," Science 261:585–588 (1993).
W. Müller et al. "Attempts to Mimic Docking Processes of the Immune System: Recognition Induced Formation of Protein Multilayers," Science 262:1706–1708 (1993).
Bhattacharjee et al., Visual Conformational Transitions of Water Soluble Polydiacetylenes: Effects of pH and Electrolyte on Absorption and Fluorescence Spectra (1980) *J. Chem. Phys.*, 73(3):1478–1480.
Chance et al, Thermal Effects on the Optical Properties of Single Crystals and Solution–Cast Films of Urethane Substituted Polydiacetylenes (1979) *J. Chem. Phys.*, 71(1):206–211.
Day et al., Polymerization of Mono– and Bi–Functional Diacetylene Derivatives in Monolayers at the Gas–Water Interface (1979) *Israel J. of Chem.*, vol. 18:325–329.

(List continued on next page.)

*Primary Examiner*—Carol A. Spiegel
*Attorney, Agent, or Firm*—Flehr Hohbach Test Albitton & Herbert LLP

[57] ABSTRACT

Bioelectronic sensors are provided employing a thin surfactant polymeric electrically conducting layer to which may be bound members of specific binding pairs. Binding of an analyte or a reagent to the specific binding pair member layer may change the electrical, optical, or structural properties of the layer for measurement of analyte. The change in the polymeric layer provides for a sensitive measurement.

5 Claims, 3 Drawing Sheets

OTHER PUBLICATIONS

Kanetake et al., Absorption and Fluorescence Spectra Polydiacetylenes (4BCMU and 3BCMU) in Solution (1985) *J. of the Phys. Soc. of Japan,* vol. 54, No. 10:4014–4026.

Fouassier et al., The Photochemistry of the Polymerization of Diacetylenes in Multilayers (1979) *Israel J. of Chem.,* vol. 18:227–232.

Kuo et al., Free Standing Polydiacetylene Films Cast from Bilayer Membranes (1988) *J. Am. Chem. Soc.,* 110:7571–7521.

Mino et al., Photoreactivity of 10, 12–Pentacosadiynoic Acid Monolayers and Color Transitions of the Polymerized Monolayers on an Aqueous Subphase (1992) *Langmuir,* 8:594–598.

Mino et al., Analysis of Color Transitions and Changes on Langmuir–Blodgett Films of a Polydiacetylene Derivative (1991) *Langmuir,* 7:2336–2341.

Olmsted III et al., Fluorescence of Polymerized Diacetylene Bilayer Films (1993) *J. Phys. Chem.,* 87:4790–4792.

Tieke et al., Polymerization of Diacetylenes in Multilayers (1979) *J. of Polymer Science: Polymer Chem. Ed.,* vol. 17:1631–1644.

Aime et al., Study of the Pressure Effect on Polydiacetylene in Good Solvent (1991) *Synthetic Metals,* pp. 41–43:203–207.

Batchelder et al., A Compact Raman Microprobe/Microscope: Analysis of Polydiacetylene Langmuir and Langmuir–Blodgett Films (1991) *Makromol. Chem. Macromol. Symp.,* 46:171–179.

Chu et al., Chromatic Transition of Polydiacetylene in Solution (1991) *Acc. Chem. Res.,* 24:384–389.

ANALYTE DETECTION THROUGH OBSERVED OPTICAL MODULATION OF POLYMERIZED LIPID LAYERS

CROSS-REFERENCE TO RELATED APPLICATIONS

This application is a continuation of application Ser. No. 08/149,075 file Nov. 9, 1993, now abandoned, which application is a division of application Ser. No. 07/893,563, filed Jul. 3, 1992, now abandoned; which application is a continuation of application Ser. No. 07/453,784, filed Dec. 20, 1989, now abandoned, which application is a continuation-in-part of application Ser. No. 07/366,651, filed Jun. 15, 1989, now U.S. Pat. No. 5,156,810.

INTRODUCTION

1. Technical Field

The field of this invention is bioelectronic and/or biooptical sensors using an electrically conducting polyunsaturated organic polymer.

2. Background

The medical field has undergone enormous expansion in its ability to diagnose and treat diseases. This expansion has brought with it a concomitant cost which has been rising at a substantially increasing rate. A significant contributor to the cost of treatment is the use of diagnostic assays to diagnose disease, monitor the treatment of the disease, and monitor the host response to the disease and the state of health during recovery. Costs associated with diagnostic assays involve sample handling, pre-treatment, reagent costs, equipment costs, and the like. All of these aspects are under scrutiny as to how they may be improved to reduce cost, to enhance sensitivity, to provide for greater flexibility in making determinations, and to simplify protocols, to mention only a few aspects.

One of the areas which has been substantially investigated is the use of semiconductor devices, where an electrical signal from the semiconductor may be related to the amount of analyte in the sample. See for example U.S. Pat. No. 4,704,353 and EPA 87/305,456 There are many problems associated with using semiconductors, such as corrosive effects of water, insulation from the aqueous environment of electrical connections between the semiconductor and electric contacts, background noise, complicated assay protocols, and the like. The semiconductor based sensors provide many attractive features, such as flexibility, high sensitivity, response to a variety of signals, and the like. Thus, there is an ongoing interest in being able to develop new sensors which can be based on relatively inexpensive materials, provide flexibility and sensitivity, while at the same time reducing the overall cost and increasing the overall simplicity of a determination.

3. Relevant Literature

U.S. Pat. No. 4,489,133 and EPA 0,274,824 describe procedures and compositions involving orderly arrays of protein molecules bound to surfactants. Lochner et al., *Phys. Status Solidi* (1978) 88:653–661 describes photoconduction in polydiacetylene multilayer structures and single crystals. Sugi, *J. Molecular Electronics* (1985) 1:3–17 provides a review of Langmuir-Blodgett film use in electronics. Reynolds, ibid (1986) 2:1–21 describes conducting organic polymers. Wilson, *Electron, Letters* (1983) 19:237 describes the principles of a three dimensional molecular electronic memory employing polydiacetylene crystals or Langmuir-Blodgett multilayer films. Descriptions of electronic devices employing organized macromolecular ensembles formed with surfactant layer crystallization include: Arrhenius et al., *Proceedings National Academy Science USA* (1986) 83:5355–5359; Haddon and Lamola, ibid (1985) 82:1874–1878; Paleous, *Chem. Soc. Rev.* (1985) 14:45–67; Vandevyer et al., *Journal Chem. Phys.* (1987) 87:6754–6763; U.S. Pat. No. 4,624,761; Fujiki, et al. *Amer. Chem. Society* (1988) 4:320–326; Biegajski et al., *Amer. Chem. Society* (1988) 4:689–693; Pecherz et al., *Journal of Molecular Electronics* (1987) 3:129–133; Lando et al., *Synthetic Metals* (1984) 9:317–327; Day et al., *Journal of Applied Polymer Science* (1981) 26:1605–1612; Shutt et al., *Amer. Chem. Society* (1987) 3:460–467; Dhindsa et al., *Thin Solid Films* (1988) 165:L97–L100; Metzger et al., *Amer. Chem. Society* (1988) 4:298–304; Fujiki et al., *Amer. Chem. Society* (1988) 4:320–326; Wohltjen et al., *IEEE Transactions on Electron Devices* (1985) 32:1170–1174; Werner et al., *Semiconducting L-B Films* (1984) 5:157–164; Sugi et al., *Thin Solid Films* (1987) 152:305:326; and Peterson, *Journal of Molecular Electronics* (1986) 2:95–99. Descriptions of methods for immobilizing biological macromolecules on polymerized surfactant films include: O'Shannessey et al., *J. Appl. Bioch.* (1985) 7:347–355; Hashida et al., *J. Appl. Bioch.* (1984) 6:56–63; Packard et al., *Biochem.* (1986) 25:3548–3552; Laguzza et al., *J. Med. Chem.* (1989) 32:548–555; Jimbo et al., *Journal of Molecular Electronics* (1988) 4:111–118; Hanifeld, *Science* (1987) 236:450–453; Goundalkar, *Communications* (1984) 36:465–466; and Cress et al., *Amer. Biotec. Lab.* (February 1989) 16–20. Bioelectronic sensors employing surfactant layer crystallization are described by Oewen, *Ann. Clin. Biochem.* (1985) 22:555–564 and Thompson and Krull, *Trends in Anal. Chem.* (1984) 3(7):173–178. Methods employing the strept/avidin/biotin binding pair for a variety of purposes have been described by: Green, N. M., *Adv. Protein Chem.* (1975) 29:85–133; Porath, J., "Nobel Symposium 3, Gamma Globulins" (J. Killander, ed.), p. 287; Almquist & Wiksell, Stockholm and Wiley (Interscience), New York, 1967, P. Cuatrecasas and M. Wilcheck, *Biochem. Biophys. Res. Commun.* (1968) 33:235; Delange, R. J., Huang, T. S. *J. Biol. Chem.* (1071) 246:698; Bayer, E. A., Wilcheck, M., *Trends Biochem. Sci.* (1978) 3:N257; Hofmann, K., Titus, G. Monibeller, J. A., Finn, F. M. *Biochemistry* (1982) 21:978; *J. Biol. Chem.* (1980) 255:5742; Skutelsky, E., Bayer, E. A., *Biol. Cell.* (1979) 36:237; Swack, J. A., Zander, G. l., Utter, M. F., *Anal. Biochem.* (1978) 87:114; Green, N. M. *Adv. Protein Chem.* (1975) 29:85; Paton, W. F. Liu, F., Paul, I. C. *JACS* (1979) 101:996,1005; and Kendell, C., Lonescu-Matiu, I., Dreesman, G. R., *J. Immunol. Methods* (1983) 56:329.

SUMMARY OF THE INVENTION

Bioelectronic sensors are provided predicated on an electrically conducting surfactant organic layer supported by an electrically insulating substrate. The surfactant layer is functionalized to allow for complex formation between specific binding pair members. By employing a variety of labels or particular organizations of the surfactant layer, binding of a specific binding pair member to the surfactant layer results in a change in an observed electrical or optical signal. The changes in the signal may be related to the amount of analyte in a sample. Bioelectronic devices are designed comprising an electrically insulating substrate, an electrically conductive organic layer, an electrode array in electrical contact with the electrically conducting organic layer, and insulation for protecting the electrodes from contact with sample medium.

DESCRIPTION OF SPECIFIC EMBODIMENTS

Figure 1:
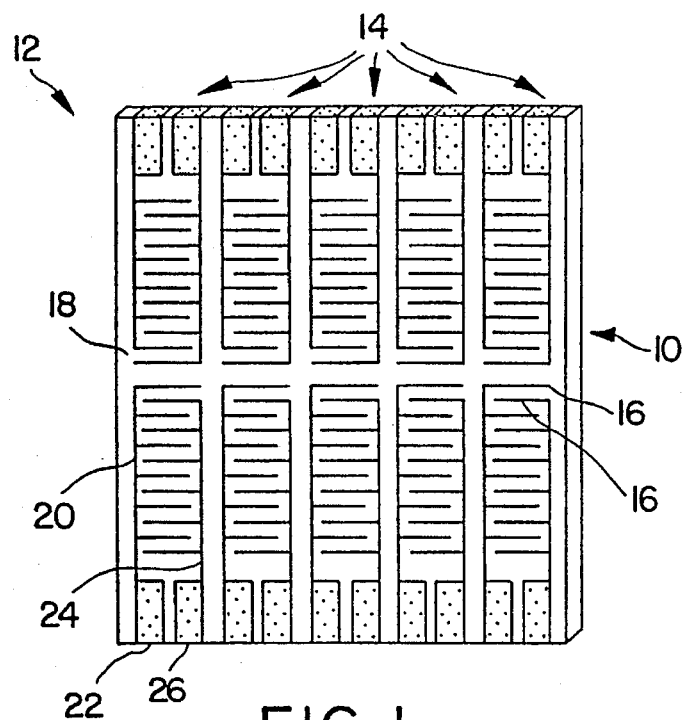
FIG. 1 is a schematic plan view of the electrode pattern.

The bioelectronic sensor devices are comprised of (1) an electrically insulating solid support or substrate, (2) a highly oriented polymerized surfactant film which is electrically semiconducting or variably conducting as a result of the polymerization, and (3) distal from the support, a member of a specific binding pair joined to the surfactant molecules, wherein the specific binding pair member is used for linking to a molecule. The molecule relays a change in the electromagnetic, e.g., electrical or optical properties of the polymer, when such molecule is bound, either directly or indirectly, to the surfactant bound specific binding member. In addition, electrode arrays are provided, which are insulated from the sample medium while in electrical conducting relationship with the polymeric layer.

The surfactant layer comprising the polymeric surfactant and its attachment to the insulative solid support will be considered first. The surfactant layer may be a "homogenous" layer in having all of the surfactant polymerized or may be a heterogeneous layer, where only a portion of the surfactant layer is polymerized. Depending on whether the surfactant layer is bound covalently or non-covalently to the electrically insulative substrate, the chemistry of the surfactant will vary. Where the surfactants are bound covalently to the substrate, the surfactant will have a group proximal to the terminus of the surfactant capable of reacting with the substrate layer.

Any of a number of different functional groups may be employed depending upon the underlying substrate. For example, where the underlying substrate is a silicate, such as glass, chlorotrialkylsilanes or silylethers may find use for binding to the glass. Alternatively, the glass may be silanated, so as to provide for active groups on the glass, such as an active halogen, which will then be reacted with amines or hydroxyl groups which are present on and proximal to the terminus of the surfactant.

Agents used for the alkylation of the glass sensor surface are typically silane compounds containing at least one reactive chloro group. Hydroxyl moieties on the glass surface displace the chlorine by a nucleophilic substitution reaction to form an irreversible covalent bond. Silanization procedures employed are similar to those previously described (Sagiv, J., *JACS,* (1980) 102(1):92–98 and Maoz, R. and Sagiv, *J. Coll. Interf. Sci.* (1984) 100(2):465–496). Silanizing agents usually include silanes quaternized with two methyl groups, a reactive chlorine and the hydrophobic hydrocarbon surfactant side chain. Examples include dimethyloctadecylchlorosilane, dimethyloctylchlorosilane, diethyldecylchlorosilane, trihexylchlorosilane, trichlorododecylsilane, trichlorohexadecylsilane, or the like.

The silanization reagent may also contain a polymerizable diacetylenic group within the hydrocarbon chain. Upon silanization with the diacetylenic agent, and subsequent addition of diacetylenic surfactants having a specific binding member, the silanized layer can be polymerized. In this configuration, the polymerized layer may be covalently coupled to the insulating glass substrate providing for a durable, high performance device. The polymerized diacetylenes provide polymeric alkadienes.

Important features of the polymerizable silanization agent include: a flexible linker between silicon and the hydrocarbon chain, optimally, a flexible hydrophilic linker attached to the end of the hydrophobic hydrocarbon chain, and one member of a binding pair attached to the end of the hydrophilic linker.

There are several major advantages to using polymerizable silanizing agents. First, the polymerizable films can be self-assembled and cast from an organic solution, avoiding the more difficult task of film formation at the air/water interface. Second, irreversibly covalently coupled films are highly stable as compared to transferred monolayers. Third, the crystalline quality of the film can be controlled by standard physical means including subphase solvent composition, superphase solvent vapor composition and pressure, average temperature, annealing through time temperature sequences, time varying temperature gradients, (analogous to zone refining techniques) where temperature can be fixed by thermal conductive mechanisms, radiant energy transfer (IR, visible, or microwave laser scanning) or frictional transfer through coupled acoustic waves or bulk compression or shearing movement. Heat can be injected into the surfactant film or into the subphase by various means.

Organic polymeric substrates may be employed, such as polystyrene, which may be functionalized without affecting the clarity of the polystyrene. See, for example, Canadian Pat. No. 1,242,862. Various groups may be introduced onto the polystyrene, such as active halogen, amino, hydroxy, or the like.

By having various groups, such as hydroxy, carboxy, aldehyde, or the like, various linkages may be made, such as ethers, esters, amides, amino, etc. The particular choice of substrate and functional groups will vary depending upon the nature of the substrate, convenience, the nature of the surfactant, the density of binding, and the like.

Alternatively, instead of having covalent binding to the electrically inert substrate, one may have non-covalent interaction. For example, polymerized bilayers may be used in an approach which eliminates the need for alkylating the glass surface Initially, one polymerized layer containing no binding pair can be placed or transferred onto the electrode substrate with the hydrophilic surface of the bilayer directly contacting the hydrophilic surface of the electrode substrate. A second monolayer is transferred to the electrode substrate such that the hydrophobic surface of the second monolayer attaches directly to the hydrophobic surface of the initial monolayer. The second monolayer contains a specific concentration of a surfactant comprising the specific binding pair member.

This device is found to be highly stable to fluid placed on the electrode substrate, fluid flowing rapidly over the electrode substrate, organic solvents, intense gaseous flows, and the like.

The bilayer configuration is useful for biological measurement because the bilayer appears much like a biologic cell membrane to biologic solutions and analytes. The film is, therefore, inert to non-specific binding events and passive except for the presence of a binding pair member which is selective for its pairing partner, for example, biotin which is selective for strept/avidin.

Of course, the bilayer configuration is not required. One can provide for direct transfer of the electrically semiconductive lipid surfactant to the substrate covering the electrode configuration bound to the substrate. And, one can provide for coating the electrically insulating substrate with the electrically conductive polymer, followed by superimposing electrodes onto the electrically conductive polymer. The latter may also be accomplished by vapor depositing or printing metal electrodes over the pre-transferred polymer film.

The lipid portion of the molecule will normally be an alkylenediyne, usually having at least 6 carbon atoms, more usually at least 8 carbon atoms, and not more than about 60 carbon atoms, usually not more than about 50 carbon atoms, where the acetylenic groups are in conjugation and will usually be at least about 2 carbon atoms from either end of the chain, preferably in the middle, or proximal to the end adjacent to the underlying substrate. The hydrocarbon chain may contain more than one diyne moiety (for example see P. S. Sotnikov et al., *J. Mol. Electronics,* (1989) 5:155–161).

Between the lipid portion of the molecule and the specific binding pair member, will be either a bond or a linking member. The linking member serves a number of functions in providing for flexibility between the aligned lipid layer and the specific binding pair member. By varying the linking member, one can provide for greater or lesser rigidity or flexibility of the specific binding pair member, in addition to increases or decreases in distance between the specific binding pair member and the electrically conducting polymer. The choice of linking member will depend upon the degree to which one wishes to perturb the electrical properties of the polymer. The more rigid and shorter the linker, assuming high affinity analyte binding, the greater the perturbation of the polymer upon binding of the specific binding member to its complementary member. Also, the linking member may be hydrophilic, hydrophobic or amphipathic. Where one wishes the linker to associate with the lipid layer, one may choose a lipid linker. Where one wishes the specific binding pair member to be relatively free in solution, a hydrophilic or amphipathic linker may be employed.

The linkers may take many forms, any type of molecule being useful depending upon its specific purpose. Thus, the linker may be comprised of carbon, hydrogen, oxygen, nitrogen, sulfur, phosphorus, halogen, metal, or the like. For the most part, the linker will be neutral. Functionalities may include oxy, amino, thio, dithio, keto, carboxamido, imino, hydrazine, hydrazide, combinations thereof, etc. The linker may be aliphatic, alicyclic, aromatic, or combinations thereof, e.g., aralkyl. The linker may be a bond, or have from 1 to 30, more usually from about 1 to 20 atoms in the chain. The atoms may be carbon or heteroatoms. The chain may be straight or branched chain, usually straight.

The linker chain may include an electrically donating or accepting molecule. The orientation of the acceptor or donor molecule (dopant) with respect to the polymer lattice will affect the polymers' net electrical characteristics. The electrical properties of the film will be affected by analyte binding where the binding event causes a change in the orientation of the dopant molecule. Doping agents may include halides, quinones, TCNE (tetracyanoethylene) or TCNQ (tetracyanoquinone) salts and derivatives thereof, conjugated molecules, antimony pentafluoride, osmium tetroxide, metals, salts or the like.

For the most part, the lipid compounds will have the following formula:

$$(A)_a(D)_aC_x(C\equiv C)_nC_yLB \qquad \text{I.}$$

wherein:

A is a functionality for linking to the underlying substrate;

a is 0 or 1;

C intends carbon;

x and y are usually at least 1, although either may be zero, and the sum of x and y is in the range of 2 to 56, more usually 4 to 32;

n is at least 2, but may be 4 or even greater;

D and L are a bond or linking group, generally having not more than about 30 atoms in the chain, usually neutral, preferably uncharged;

B is a specific binding member, where B and its complementary member have an affinity of at least about $10^{-9}$ preferably at least about $10^{-10}$ as measured by equilibrium dialysis or the like.

Complementary binding members include: biotin and avidin or streptavidin (both indicated together or strept/avidin), dihydrofolate reductase and methotrexate, homologous nucleic acids of at least 12 nucleotides, or the like. The significant factor is that the specific binding pair members will provide stable non-covalent binding during the course of use of the subject device.

The linker arm may be lengthened to enhance the degree of protein binding in the protein layer. The flexibility of the linker arm will also influence protein binding. The use of rigid linkers such as polypeptides rich in proline reduces the spatial degree of freedom that the specific binding pair member can undergo. Linkers such as polyethylene oxide or polypropylene oxide or combinations thereof provide significantly greater freedom of position and orientation of the specific binding pair member. Hydrophobic linkers, such as polyethylenes, tend to constrain the specific binding member close to the lipid surface. Hydrophilic linkers, such as polyethers and peptides, facilitate binding through interactions between the specific binding pair member and the aqueous subphase (to be described subsequently).

Compounds of interest include: biotinamidocaproylethylenediamine- 10,12-pentacosadiynamide, 25-dimethylchlorotetraethyleneoxide-10,12-pentacosadynoate-tetraethyleneoxide-biotin, α-galactose-1,4-β-galactose-glycosylamido-10,12-pentacosadiynamid-25-tetraethyleneoxide-dimethylchlorosilane.

In preparing the subject compounds, various unsaturated surfactants may be employed. Exemplary surfactants include: 2,4-tricosadiynoic acid, ethanolamine 10,12-pentacosadiynamide (EA-PDA), 10,12-nonacosadiynol, 2-hydroxyethyl octadeca-8,10-diynoate, eicosa-12,14-diynyl-10,12-phosphatidyl serine, pentacosa-10,12-diynoic acid, tricosa-10,12-diynoic acid, ω-aminopentacosa-10,12-diynoic acid, as well as other di- or polyacetylene compounds with one to two functional groups for linking to the specific binding pair member, the underlying substrate, or other polymer forming surfactants, including single or double or greater acyl chain polymerizable surfactants. These polymerizable intermediate surfactants or filler surfactants may also serve in the preparation of the polymeric layer to control the density of the specific binding pair member at the surface of the layer. Thus, one may vary the number of specific binding pair member molecules at the surface, by employing surfactants which are capable of copolymerization, but have not been joined to a specific binding pair member. Filler surfactants may be modified with an electron donating group, e.g., S, N, P containing group, etc., for the purpose of chemically doping the semiconducting polymer film.

An alternative way for reducing the level of specific binding pair member at the surface is to use surfactants as diluents for the polymerizable surfactant, which also serve as filler surfactants. These surfactants may be naturally occuring, synthetic or combinations thereof and may be illustrated by laurate, stearate, arachidonate, cholesterol, bile acids, gangliosides, sphingomyelins, cerebrosides, glycerides, or the like. These surfactants may be present in from about 0.1 to 75 mole percent, usually 1 to 5 mole percent.

The subject compositions which form the electrically conducting polymer and contain the specific binding pair member may be readily prepared in accordance with conventional procedures. For example, the diynoic acid may be activated with an appropriate carbodiimide and then combined with the specific binding pair member joined to a linker group, for example, an alkylenediamine where one of the amino groups is linked to the specific binding pair member. Alternatively, one may combine the activated diynoic acid with the linking group followed by reaction of the remaining functionality of the linking group with the specific binding pair member. The particular order in which the various components are joined will depend to a great degree on the nature of the functionalities, the nature of the specific binding pair member, and convenience.

Of particular interest as the specific binding pair is biotin with strept/avidin. In this manner, the strept/avidin may bind to two biotins on the surface and may be tightly linked to the lipid polymer, while still retaining two sites for further biotin binding. The biotin binding sites facing away from the surface of the polymer are free for subsequent binding by a variety of biotinylated analyte molecules.

Molecules which may be derivatized with biotin, covalently or non-covalently, for the purpose of binding analytes to the polymer surfactant layer include: small mono- or multivalent antigens (for antibody binding), receptors (for specific analyte binding), single strands of nucleic acid (for binding complementary strands), protein A (for the subsequent binding of antibodies through their Fc receptor), lectins, mono- and oligosaccharides, drugs, hydrazines for chemically coupling reactive molecules, enzymatically cleavable compounds, such as prodrugs, and mono- and polyamino acids.

Strept/avidin may be complexed directly to an analyte binding molecule, either covalently or non-covalently. This approach avoids the use of biotin in an intermediate binding pair. Examples of molecules which may be linked to strept/avidin include: protein A, antigens, antibodies, antibody fragments and natural receptors.

An alternative approach involves the use of genetically engineered hybrid molecules of strept/avidin fused with a binding protein. Examples of proteins suitable for hybrids which may be used include: protein A, antibody molecules, fragments and hybrids, receptors, enzymes, toxins, or the like. Because the crystallographic structure of the strept/avidin/biotin complex has been resolved by two-dimensional electron crystallography and three-dimensional x-ray crystallography, a rational approach to designing a binding pair combination aimed at optimizing bioelectronic sensor performance may be taken.

Various members of binding pairs may be complexed with colloidal metal labels such as gold, silver, tungsten, or the like. The presence of metal particles or clusters will alter polymer film conductivity through close interaction with the conducting polymer backbone. Reorientation of the metal particles with respect to their proximity to the polymer backbone upon analyte binding, where steric strain of analyte binding causes a repositioning of the metal particles, may be used as a signal amplification mechanism. Repositioning of a large metal complex with respect to the polymer results in a significant change in the local resistivity compared with the reorientation of a small non-metallic organic molecule. Where the particle is ferromagnetic, the particle will have a significant effect on the polymers' net magnetic dipole moment.

Of particular interest is analyte binding to a receptor where the receptor is biotinylated and bound to strept/avidin which had been pre-bound to the biotinylated polmer. Direct binding will usually be covalent, while indirect binding will usually be non-covalent. Receptors of particular interest will be antibodies, which include IgA, IgD, IgE, IgG, and IgM, which may be monoclonal or polyclonal. The antibodies may be intact, or with their intermolecular sulfhydryl bridges totally or partially cleaved, e.g., monovalent antibody fragments (a single heavy and light chain) fragmented to F(ab')$_2$ or Fab; or the like. The intact or cleaved antibodies may be used to make a recombinant protein A-antibody or single heavy-light chain hybrid. Coupling of biotin through the antibody's oligosaccharide moiety to hydrazines can be achieved with the intact, partially, or totally cleaved antibody. Maleimide linkages may be used for the intact, partially, or totally cleaved antibodies and the F(ab')$_2$ fragment, while the Fab fragment may be engineered into an antibody hybrid. Other examples of antibody coupling to polymer films will include the use of recombinant hybrid linker proteins and recombinant antibody molecules. Antibodies functionalized and immobilized at the Fc portion will ensure the availability of the binding sites for further binding.

Also of interest is the hybridization of single stranded DNA or RNA molecules where the molecules are either covalently attached to the polymers' hydrophilic surface or attached to the surface through the strept/avidin/biotin binding pair. Direct measurement of polynucleotide hybridization is important because it eliminates the need for intermediate amplification steps and provides for extreme specificity. A large range of different microorganisms carrying common surface antigens may be differentiated using hybridization methods, whereas antibody-antigen detection methods may be limited by cross-reactive binding events or the difficulty in obtaining sufficient quantities of antigenic material.

The use of bioelectronic sensing methods may be used for the immediate detection of oligonucleotides purified directly from microorganisms after the oligonucleotide has been enzymatically amplified in numbers, e.g., using PCR. For covalent coupling of oligonucleotides to the polymer surface, the nucleotide may either be linked to the monomeric surfactant prior to polymerization of the film or attached to reactive groups on the surface of polymerized films. The latter has the advantage of preforming high quality polymer films with small purified momomers where the initial attachment of the oligonucleotide to the monomer creates a surfactant monomer with an exceedingly large polar head group which negatively influences high quality film formation.

Covalent attachment of the oligonucleotide to the surfactant may be accomplished through standard chemistries used for solid phase immobilization and affinity chromatography. For example, periodate-oxidized nucleotides may be attached to hydrazide groups which have been incorporated into the polymer film. Coupling can be carried out under conditions which are fast, mild, and give high yield (R. Lamed, Y. Levin, and M. Wilchek, *Biochem. Biophys. Acta*, (1873) 204:231). The oligonucleotide may be coupled to the polymer with the use of other chemical coupling reagents either through the 3' or 5' end of the molecule or to other reactive moieties along the length of the molecule.

Non-covalent attachment of the oligonucleotide to the surfactant surface can be accomplished using the biotin-avidin binding pair. Biotin is covalently coupled to a nucleotide positioned anywhere along the oligomer chain. The biotinylated oligomer is attached to the polymer-surfactant surface through strept/avidin where the polymer film has also been derivatized with biotin. At this point the bioelectronic sensor consists of biotinylated polymer film, polymer bound strept/avidin, and strept/avidin bound biotinylated oligonucleotide.

During an assay measurement, the oligonucleotide from a microorganism is presented to a bioelectronic sensor which contains a complementary base pair sequence on the sensor surface. Temperatures and media are controlled to ensure that hybridization takes place. Hybridization, helix formation, and super-helix formation have a direct structural effect on the surfactant-polymer surface. The effect can be amplified by the addition of double stranded oligonucleotide binding proteins. For example, nucleosomes may be added to induce coiling of the oligomer and unwinding proteins may be added to uncoil duplex hybrids. These structural changes directly affect the polymer lattice orientation, and thickness of the sensor film and can be measured using optical or electronic methods.

The specific binding pair member layer which becomes bound to the lipid-bound complementary member of the specific binding pair will form a layer, which may be crystalline or non-crystalline, where the molecules may be contiguous or non-contiguous. The nature of this layer will be controlled to a great degree by the linking unit which covalently links the specific binding pair member to the surfactant. The ratio to which the surfactant-bound specific binding pair member is bound to surfactants which are free of such member will be a function of the size, character and nature of the non-covalently bound reciprocal member, as well as other considerations on a case by case basis. Particularly, for proteins, crystal layers can be achieved where the protein is present in a substantially contiguous relationship. An example is the combination of biotin as the surfactant-bound member and strept/avidin or avidin as the non-covalently bound member. This combination has a number of advantages. First, the biotin-avidin combination has a very high binding affinity, approximately $10^{-14}$M. Furthermore, it is believed that the organization of avidin will provide for two biotins to bind to the avidin on one side of the avidin molecule, leaving two binding sites free and exposed to the medium. Therefore, by having biotin attached to a variety of moieties, molecules, particles or the like, one can provide for binding of such moieties to the avidin bound to the surfactant layer. Thus, one can provide for conjugates which allow for additional specific binding pair members to become bound to the surfactant layer through the intermediacy of the biotin-strept/avidin link. In this way one can provide for various competitions between a biotin conjugate and an analyte for a receptor, where a binding of the receptor to the biotin conjugate inhibits binding to the strept/avidin, or other protocols which allow for the detection of an analyte of interest.

Electronic Element

The subject electronic elements may be prepared in a variety of ways and have a variety of configurations. Particularly, the electronically conductive polymer may be provided as a coating on the electrically non-conducting substrate followed by the formation of electrodes over the polymer, or electrodes may be formed on the non-conducting substrate, followed by coating with the electrically conducting polymer. Mass production methods for electrode formation may be accomplished by various positive and negative photoresist methods or by fine conductive ink line extrusion methods. The electrically conducting film is referred to as "variably conducting," since the conductivity of the film may range from the conductivity of a semiconductor to a conductivity approaching that of a metal.

Electrode/Substrate Formation

Various techniques may be used for preparing electrodes on the substrate or on the lipid layer coated on the substrate.

For the negative photoresist lift off method, a smooth substrate, e.g., glass, usually 0.1–5.0 millimeters thick, is coated with a negative photoresist. A photolaser-plotter acetate master, Linotronic acetate master, or chrome master is overlaid and the photoresist is exposed to intense light and then the resist is developed to remove the non-exposed areas. Upon development, a thin metal layer (chrome) usually 100–1,000 Angstroms thick is vapor deposited over the photoresist. Deposition of tungsten and then silver alloy or other metals may follow the chrome deposition. The "metallized" substrate is then developed to "lift off" all remaining photoresist. The desired metal traces are left on the substrate surface. The final electrode sheets are thoroughly washed and are subsequently surface treated.

Another method for preparing electrodes involves coating a glass or other inert substrate with a metal to create a front surface coat. Typical metals include chrome; silver; gold; platinum; nickel; alloys; and oxides such as indium tin oxide, conducting polymers, and inorganic substances. A photoresist film, negative or positive, is deposited over the coat by spraying, laminating, dipping, or the like, onto the metal or other surface. A master pattern is created by computer-aided design using high resolution techniques and placed over the photoresist coat. Illumination or photactivation with UV or white light, depending on the film composition, may be employed. The photoresist is then developed, using developing reagents such as caustic soda to remove the unexposed areas of a negative photoresist. Chemical etching will subsequently remove the exposed metal from the glass surface. Cleaning off residual photoresist material may be accomplished using 10% NaOH for 3–5 minutes. The rinse steps include 10% detergent, rinsing 2–3 times in 10–20 megaOhm water, and then rinsing in high purity water and organic solvents. The electrode may be heated to remove any surface water. Heating is accomplished using a dust-free oven purged with inert gas, e.g., nitrogen, at temperatures ranging from 30°–150° C. for between 30 seconds to 1 hour. The glass surface is then treated for transferring polymer films. Subsequently, the polymeric film prepared as described below is then transferred to the substrate-electrode so as to overlap the electrodes. Transfer is achieved by methods described below.

As described previously in greater detail, for fixing the lipid layer to the substrate, various techniques may be used. For the glass substrate, silanization finds use, where the lipid has a silylhalo group proximal to the terminus of the lipid molecule distal from the specific binding pair member.

Polymerized bilayers may be used as an alternative approach to silanization. For bilayer formation, initially, one polymerized layer containing no binding pair can be placed or transferred onto the electrode chip with the hydrophilic surface of the bilayer directly contacting the hydrophilic surface of the electrode chip (glass surface). A second monolayer is tranferred to the electrode chip such that the hydrophobic surface of the second monolayer attaches directly to the hydrophobic surface of the initial monolayer. The second monolayer contains a specific concentration of a surfactant comprising the specific binding pair member.

The bilayer configuration is very useful for biological measurement because the bilayer appears much like a biologic cell membrane to biologic solutions and analytes. The film is, therefore, inert to nonspecific binding events and very passive except for the presence of biotin which is very selective for strept/avidin.

Any number of monolayers may be transferred to the substrate. Successive layers are juxtaposed with like surfaces facing each other, i.e., the hydrophilic surface of one layer facing the hydrophilic surface of the next layer and the hydrophobic surface of each layer facing the hydrophobic surface of the neighboring layer. Layers may be the same or may be composed of differing monomers, dopants, binding pairs, or be polymerized to a differing extent or at different bonding sites. Successive layers may be modified before or after polymerization or after transfer to the substrate.

In order to provide a substantially uniform polymerized electrically conductive surfactant layer, the surfactant layer is formed on an aqueous subphase. While various techniques have been employed for polymer film formation, the following procedure has been found to have numerous advantages.

Polymer Film Formation and Quality Control

In a particular embodiment, the aqueous subphase is prepared by applying 1.5 ml 5% DMSO and 95% 18 megaOhm water (room temperature) to a 1"×3"×0.04" microscope slide (Scientific Products) which had been pre-cleaned in KOH/ethanol and extensively rinsed. The subphase is spread evenly over the surface, and the slide is then traversed to a hot aluminum block and heated to 100° C.

A surfactant solution (30 μl at a concentration of 2 mM in a spreading solvent; chloroform/hexane/methanol 25/25/1 v/v/v with a conjugated specific binding pair ("sbp") member is atomized onto the subphase surface. Various ratios of ("sbp") free member surfactant and sbp member surfactant conjugate may be employed. The solvent evaporates immediately forming a "fluid" surfactant film.

The surfactant solution may be spread on the preheated aqueous subphase to facilitate evaporation of the solvent or melting of the surfactant. Atomization using conventional atomizers, air brushes or sonic nozzles may be employed to facilitate addition of the surfactant to the monolayer.

Upon complete evaporation of the solvent, the microscope slide is smoothly traversed into a cooling chamber. The traverse rate is a critical parameter for high quality film formation and is controlled with high precision. The subphase is maintained at the lower temperature for a sufficient time for the temperature to equilibrate and then irradiated with UV light (254 nanometers, 1.5 inches above subphase, UVG-54 mineral light, UVP Inc., San Gabriel, Calif.). After polymerization, the slide is transferred from the crystallization chamber and the film quality is inspected using fluorescence and polarizing microscopy.

A crystallization chamber provides for a heating chamber and a cooling chamber, where the time spent in the heating chamber, the time for transfer from the heating chamber to the cooling chamber, and the time spent in the cooling chamber, as well as the temperatures of the various regions, is readily controlled. The temperature in the heating chamber is varied, depending upon the nature of the subphase. Usually, the temperature should be at least about 10° C. below the boiling point of the subphase composition and 10°–30° C. above the melting temperature of the surfactant. The temperature will usually be about 100° C. The time spent in the heating chamber will be sufficient to ensure the complete fluidity of the surfactant. Generally, the time will be in the range of about 10 sec to 4 minutes, to ensure complete dispersion of the surfactant. The transfer time from the hot chamber to the cold chamber will generally be from about 1 to 5 min. Slow movement of the subphase carrier through the various regions will generally be about 1 to 3 inches per minute in traversing the hot chamber and going to the cold chamber, while fast movement into the hot and out of the cold chambers will generally be greater than about 10 inches per minute. Traverse rates from the hot to cold chambers will vary depending on the subphase depth, the partition distance between the hot and cold blocks, and the melting temperature of the surfactants employed. In the cooling chamber, the temperature will be less than the melting temperature of the surfactants, preferably less than about 10° C., and may be as low as −10° C. or lower, depending upon the nature of the subphase. The crystallizing time in the cooling chamber, will usually be at least about 15 sec. and not more than about 10 min., usually not more than about 5 min.

Another approach to single crystal generation is analogous to zone refinement. The surfactant film is held just below the phase transition temperature, and a band of higher temperature is repeatedly swept through the film. Impurities preferentially partition into the melted zone, thus experiencing bulk transport in the direction of the moving temperature band. This effectively moves impurities to one end of the polymer film. The temperature band can be generated by moving a heated wire above or below the film, using the superphase or subphase, respectively, as a conduction medium. Alternatively, a radiation mechanism can be used to transfer heat as a moving band to the film. The radiation can be in the IR or microwave, thus dumping heat directly into the film due to transfer of vibrational energy into thermal energy. A visible or IR laser could also be scanned across the sample, transferring thermal energy via vibrational or electronic relaxation mechanisms.

Crystal Morphology/Control

The factors that strongly influence the crystalline morphology of the films include: cooling rate, subphase composition, subphase pH, superphase composition, superphase humidity, and the like. By controlling factors which affect crystal growth and morphology, a variety of types of crystallites may be formed including: spheralytic, dendritic, and columnar.

Crystals are typically grown under conditions where the lateral surface pressure is kept constant and the temperature is varied. The use of isobaric conditions provide for the formation of extremely large crystals as opposed to those obtained by lateral surface compression. Crystals ranging from several millimeters to several inches in length are observed using isobaric conditions. Previously, others have found crystalline domains ranging up to only 3 mm in diameter by varying the lateral surface pressure [Day, D. and Lando, J. B., *Macromolecules,* (1980) 13:1483–1487].

In addition to the advantage of producing large crystalline domain sizes, the use of controlled temperature allows for simplistic fabrication procedures. A crystallizing chamber with few parts is employed and the conditions under which the crystals are formed can be highly regulated.

The bioelectronic sensors described here are typically formed with neutral surfactants such as EA-PDA as a filler surfactant. Typically, filler surfactants should be non-charged and have a polar headgroup. The advantage of using neutral filler surfactant is that it avoids the use of charged surfactants, such as long chain fatty acids, which require a counter-ion in the subphase and thus the crystal formation and procedure can be simplified over the use of charged surfactants.

The use of non-charged filler surfactants also facilitates the formation of very large crystalline domains even when the domains are co-crystals of the non-charged filler surfactant and the specific binding pair, e.g., biotin, conjugated filler surfactant. Crystals of dimensions equal to those of the filler surfactant alone are formed even in the presence of mole percentages ranging from 0.1 to 20 mole percent of the specific binding pair member conjugated surfactant.

Spheralytic crystals ranging from 1 to several millimeters across are formed under conditions of rapid cooling. Transfer rates from a hot surface where the surfactant is in a fluid state to a chilled surface where the surfactant is in a crystalline state is accomplished in a matter of seconds.

Spheralytic crystals usually form when the lateral surface pressure is relatively low during the crystallization process. Low lateral surfactant pressure is accompanied by using slightly less than saturating amounts of surfactant spread at the air/water interface. Spheralytic crystals form over subphases containing 1–5% DMSO (dimethyl sulfoxide) in water.

Larger dendritic crystals, usually 0.5 to 1.0 cm in diameter, form in slower cooling conditions with low lateral surface pressure. Reduction in the percent of DMSO in the subphase usually favors the formation of dendritic crystals over spheralytic crystals. Convection or disturbance in the superphase also favors the formation of dendritic crystals.

Large, high quality columnar crystals, usually about 0.5 to several centimeters across, up to 10 centimeters or more, are formed under moderate chilling from 110° C. to 3° C. over a period of minutes, usually fewer than about 5 min. Typically 5% DMSO in water is used in the formation of columnar crystals. It is found that high lateral surface pressure favors the formation of columnar crystals.

In addition to favoring the formation of large high quality crystalline domains, the presence of DMSO acts to extract low quality polymer blends from the polymerized film. Typically, polymerized material with a bluish tint (650 nM in the absorption spectrum) is extracted in the presence of DMSO into the DMSO water subphase. High quality polymerized film, typically light pink or red in color, remains at the air/water interface and low quality contaminants, usually blue in appearance, are extracted by the DMSO. Other chaotropics in the subphase such as DMF (dimethylformamide), urea, guanidine HCl, and other polymers such as polyethylene oxide also favor large crystalline domain formation.

The addition of non-polymerizable surfactants, such as non-volatile liquid hydrocarbons, e.g., dodecane, may also be used to increase the lateral surface pressure and enhance crystal formation. However, it is important that the non-polymerizable material laterally phase separate during the crystallization process.

The subphase composition has a significant influence over the crystalline morphologies of the surfactant layer. The subphase can be composed of pure water or a variety of water miscible organic compounds, organic polymers, chaotropic reagents, sugars, or salts. Examples include: glycerol, polyethylene glycol, trehalose, sucrose, mono- or polysaccharides, or polar organic solvents miscible with water, including DMF, DMSO, acetone, alcohols, ketones, furans, dioxane, ethanolamine, and phenols, alone, in combination, or the like. High boiling point solvents such as glycerol will prevent evaporation during heating, while low boiling point solvents will enhance the evaporation. Other organic solvents can be used to stabilize the surfactant film, particularly to promote a favorable interaction between the water and the polar headgroups, linkers, and ligands of the surfactant. The subphase may also contain organic acids, inorganic acids, or bases which affect the surfactant film through ionic interactions, i.e., charge stabilization. The ionic components may include mono- and polyvalent ions, and charged mono- and oligosaccharides, e.g., heparins and glucosamines.

The addition of DMSO to the aqueous subphase in concentrations from 0.5 to 50% provides for films superior to those formed with pure water as the subphase. The effects of DMSO are several fold. First, the films are more intact and have fewer microscopic cracks, tears, or apparent defects. Second, the crystalline domains are more tightly compacted and condensed. DMSO allows subphase temperatures to be raised above 100° C. where used prior to film crystallization and avoids the risk of boiling. The addition of ethylene glycol further stabilizes the subphase during heating. Subphase temperatures from 120° C. to 180° C. may be achieved in the presence of DMSO and ethylene glycol.

Monomeric polymerizable surfactants are spread on the subphase at a concentration ranging from 0.01 to 50 mM in the spreading solvent. Typically 0.1 to 10 mM is most useful. Films are usually formed with a mixture of polymerizable surfactants including surfactant-linked specific binding pair members and filler surfactants which have no specific binding pair member attached. A polymerizable moiety of the filler surfactant may be conveniently similar, having the same or similar chain length and functional groups, or identical to that of the specific binding pair member containing surfactant. The filler surfactant may have all the chemical characteristics of the ligand surfactant and should have polar headgroups which are biologically inert and resistant to non-specific specimen binding. As an example, the filler surfactant may have an hydroxyl, polyhydroxyl, or polyethylene oxide headgroup which acts to prevent non-specific adherence of biological matter.

The filler surfactant may also contain a chromophore for enhancing the optical visualization of the film and to enhance the photoelectrical injection of light. In addition, the filler surfactant may contain an electrical doping group to enhance the polymer film's intrinsic conductivity. Binding may affect the position or orientation of such doping groups. Thus, the doping group may act as an amplifier of protein binding. Such electrical doping groups may also be directly attached to the binding pair member surfactant for convenience or signal enhancement.

The mole percentage incorporation of the sbp member surfactant in the films affects film stability. The mole percentage generally ranges from 0.01 to 90%, more usually from 0.1–10% and usually in the range of 1.0 to 5%. The composition of the polar headgroup of the filler-surfactant can modulate the specific binding of biological material. Steric displacement can enhance protein binding, and steric hindrance could inhibit protein binding. The composition of the polar headgroup of the filler-surfactant can thus provide a control mechanism for adjusting binding affinities and interactions.

Optionally, regulation of the subphase chilling rate may be accomplished through the use of various subphase carrier plates. Often, thin metal plates, usually 0.20 to 1.0 mm in thickness, are used. Metal carrier plates can be made of aluminum, stainless steel, copper, bronze, rare metals or the like. Black anodized aluminum plates are particularly useful because they rapidly exchange heat and, when the surface finish is dull, they reflect a minimal amount of low angle light during film imaging processes. For the purpose of mass production, carrier plates may be reusable.

Thermal grease is useful as a sandwich material between the glass cover slip on which the subphase is placed and the metal carrier plate. The thermal grease serves to anchor the glass coverslip to the metal carrier and provide for rapid thermal exchange between the glass and metal.

The subphase may be placed directly on the metal thereby avoiding the use of the glass cover slip. One advantage of this is that the positioning of water, placed on the carrier may be regulated by polishing or roughing the metal surface since polished surfaces tend facilitate a high wetting angle between the subphase and the metal surface. The water tends to "bead up" on polished areas whereas toughened surfaces tend to reduce the wetting angle.

Polymerization of the surfactant layer is accomplished with ultraviolet light immediately following crystallization, but may be accomplished as the crystals are formed. The subphase temperature during this operation is usually between 5° C. and 10° C., more usually between 5° C. and 0° C. The exposure at 5 milliwatts per square centimeter is carried out for between 5 seconds and 5 min., but more usually between 25 seconds and 2 min. Other levels of light intensity may be used with adjusted lengths of exposure to ensure the desired level of polymerization. Bandpass filters may be placed between the UV source and the crystallized layer during polymerization to optimize the desirable bond formation while minimizing undesirable bond formation.

A grid mask may be placed between the ultraviolet source and the crystallized layer during irradiation to manufacture convenient shapes of polymerized surfactant. Additionally, polarizing filters may be used to regulate the degree of polymerization in crystals specifically oriented with respect to the polymer bond formation direction.

Typically, clear glass microscope slides are used for the purpose of visualizing polymerized films by direct transmitted light through the subphase. Clear microscope slides, typically 0.05 to 1.0 mm thick also serve the purpose of directly holding the subphase. Polarizing filters enhance contrast between crystalline domains. Thin glass slides provide for more efficient heat exchange.

The film quality is monitored with the use of broad band polarizing or fluorescence microscopy prior to incorporation into the bioelectronic sensor device. The criteria for high quality films include: large, regular crystalline domains (5 to 30 mm across); tight domain packing (minimal separation between crystalline domains); minimal defect within a domain (no apparent cracks); and high degree of anisotropy.

Highly crystalline polymerized films are transferred to the electrode substrate by direct horizontal contact between the substrate and subphase surface. Immediately after film transfer, the transferred films are rinsed in high purity water and dried, conveniently at 100° C. for 5 to 15 min. in a nitrogen atmosphere.

Film Inspection

Polarizing filters and visible light sources are useful for resolving crystalline domain morphologies of polymerized films at the gas/subphase interface. Two polarizing filters give maximum visual contrast of the polymerized film. One filter is placed in front of the light source prior to the light interacting with the polymerized film. The other filter is placed between the polymerized film and a viewing microscope. Rotation of either filter in a plane perpendicular to the light path between the source and the viewing microscope makes the individual polymer/crystalline domains highly visible.

The crystalline domains give rise to a variety of colors as the filters are rotated. Crystalline size, shape, defect state, orientation, and compactness is readily observed with the use of polarized light. Polymerized films may be imaged with a CCD array camera and an optical processing system. Crystalline morphology and quality can be made quantitative by image digitization and analysis. Different wave lengths of light may be passed through the films for increased contrast and for qualitative and quantitative information about the films.

Fluorescence microscopy may be used in combination with polarization for moderate resolution film inspection. Similarly, microscopic and macroscopic defects, domain size and shape, intensity, and morphology may be analyzed. Scanning tunneling, circular dichroism and optical rotary dispersion atomic force, and electron microscopy are used for inspecting film quality at high resolutions.

Once the electrodes have been formed and the electrically conducting layer placed on the substrate, it is necessary to ensure that the electrodes are protected from contact with an aqueous medium.

The photoresponsiveness of the transferred films can be spatially resolved by illuminating a small area of the film using a broadband fiber optic illuminator and recording the induced photocurrent. The entire film on the electrode substrate is scanned with an illuminated fiber optic probe by attaching the fiber to an XYZ translation stage. The recorded photoresponses at each point on the bioelectronic sensor chip is then plotted against position with respect to the electrode.

A second scanning technique is used to spatially resolve the refractive anisotrophy and therefore the crystal orientation. In this technique, a broadband source illuminates the entire sample through a polarizer. The linearly polarized light incident on the sample is made elliptical due to the highly anisotropic index of refraction of the polarized film. Because of the dispersive nature of the index of refraction, different colors (wave lengths) experience different degrees of ellipticity. A second polarizer receives the elliptically polarized light exiting the film. By rotating this second polarizer near the crossing angle, each wave length will pass with an intensity proportional to the projection of the ellipse major axis into the polarized axis of the second polarizer. The light exiting the second polarizer is directed into a monochromator and the intensity of each wavelength is recorded. By measuring the exiting light through a narrow aperture and by scanning the bioelectronic sensor chip past the aperture, spatially resolved spectra are obtained. The result is a spatial map of the size and orientation of the crystals.

Electrode Protection

Microprotection may be accomplished through the use of a computer controlled fluid dispensing device. A sample dispensing chamber (usually a syringe) is mounted on a stepper motor driven XYZ stage. A pneumatic pump, pressurized by nitrogen gas and coupled to the computer, controls the fluid protectant flow rate. The dimensions of the protective traces are controlled by protectant flow rate, Z height, needle angle, needle bevel, syringe needle diameter, XY traverse speed, ambient temperature, and protectant viscosity.

Desirable properties of protectants include: rapid curing, inert effect on the polymer/surfactant layer, non-toxic fumes, materials approved for medical diagnostic devices, electrical insulation from moisture, appropriate wetting angle, and a viscosity appropriate to spreading ultrathin traces without bleeding or wicking.

The metal electrodes can be sealed against contact with water with a variety of protectant or insulating materials. These include: parafilm, hemeseal, barge, hot wax, polymer plastics, rubber silicone, hydrocarbon polymers, polymer matrices with silica particles, rubber cement, and UV curable materials, e.g., acrylates, and cyanoacrylates, waxes, fluorinated aliphatic compounds, rubber urethanes, photoresist materials, nail polish, glues, teflons, or other commercially available sealants, tapes and adhesives. When parafilm is used, the film is placed over the electrode, gently compressed to remove any air bubbles, and then warmed to allow the parafilm to soften and coat the electrodes. The other sealants may be coated onto the electrodes and, when appropriate, the bioelectronic device warmed to allow for reduction in viscosity and rapid curing.

High resolution electrode sealing (1.0 to 50 micrometers) is accomplished by vapor deposition processes, sputtering, or the like. For protectant deposition, a stencil with openings symmetric to the metal electrode traces on the substrate, but slightly broader than the metal traces, is placed above the semiconducting polymer coated electrode surface using standard mask alignment techniques. The substrate and masks are placed in a vapor deposition apparatus and then an insulating material, such as silicon oxide, is vapor deposited in such a way that the electrode is completely coated with the insulating material. The insulating material should extend slightly past the electrode edge so that it completely isolates the electrode from the environment and leaves the polymer film between electrodes uncoated.

Simultaneous Electrode Formation and Protection

Electrode formation and protection is accomplished simultaneously by extrusion of electrically conductive inks and electrically insulating polymers. This method has several advantages: first, the polymer films can be pre-formed and transferred to insulative substrates in any orientation; second, good reproducible ohmic contact is made between the polymer and conductive ink electrode; and third, the dual process is time saving since two processes can be accomplished simultaneously.

Conductive inks are selected based on their viscosity, conductivity, curing time, stability, ability to form high resolution lines (200 microns or less), self leveling properties, and the like. Insulative polymers, as noted above must be compatible with the conductive inks. The process of electrode formation is similar to the electrode protection process above.

High quality crystalline films are transferred to insulating substrates as described above, selected for their crystalline quality, and oriented in the electrode formation apparatus. First, the dimensions and orientation of the electrode array are programmed with a computer interface. Second, thin lines of conductive ink are traced in the desired location by extrusion from a closed pressure controlled dispenser. Third, the insulative coating is extruded over the ink traces so that the ink is completely covered yet only a small margin of protective coating overlaps the edges of the ink. Finally, the ink and protectant are cured under low heat (125° C.) in an inert atmosphere to avoid damaging the polymer film.

Bioelectronic Sensor Activation

After completion of the insulation, the surfactant film may, if necessary, be activated. Activation will depend upon the nature of the molecular coupling system. At this point, the dry bioelectronic sensor device is comprised of the insulating substrate; polymer film with attached molecules for binding, e.g., specific binding pair member, parallel metal electrodes which are sealed for moisture; and metal electrically conductive leads.

The sensor surface is activated by specifically coupling, either directly or indirectly, the specific binding pair member to the polymer/surfactant surface on the electrode substrate. When the complementary member is an antibody, coupling of the antibody to the sensor is accomplished so that the binding sites of the antibody remain free to associate with specific antigens.

The magnitude of the bioelectronic sensor response may be modulated by several post-processing methods including: heat treatment, dehydration, solvent treatment, photoablation, particle beam bombardment, gas treatment, doping reagents, organic covalent derivatization or the like.

Heating significantly reduces the base line conductivity of the bioelectronic sensor while increasing the sensor photoresponsiveness. Heating the film-coated device drives off any residual surface moisture. Drying is accomplished at 50° C. to 200° C., more usually from about 90° C. to 120° C. Drying agents, a stream of inert gas, or vacuum desiccation may be employed for the same general purpose.

Solvent treatments may be used to change the optical photoresponse of the polymer containing bioelectronic chip. Non-polymerized material or contaminating material not directly associated with the polymer film may be solvent extracted. For example, prior to electrode protection, the polymer coated electrode device may be submersed in DMSO for several minutes, rinsed in DMSO, and then dried. DMSO has been found to selectively remove a visually blue grade of polymer while not affecting the higher quality pink grade of polymer. The blue grade polymer (650 nm) may also be converted to the pink polymer (500, 540 nm) by heating or extended UV irradiation (254 nm). The blue/pink color transition may be modulated by specific protein binding.

Solvent treatment of the films may also create a disordering of the organized polymer film. In some instances it may be desirable to disorder the film for the purpose of modifying the electrical properties of the film. For example, by inducing a strained state in the polymer lattice, the film may exhibit higher conductivity. Another application involves the repositioning of the bound analyte binding molecule. Disruption of the polymer lattice may provide for greater availability of the ligand for analyte binding. Polar solvents including acetone, butanol, methanol and other polar solvents have a clear effect over the fluorescence characteristics of the polymer. In a flow cell configuration, water passed over the film has no visual effect on the fluorescence intensity. On addition of acetone or butanol, the film's fluorescence decreases by two-fold. The decrease is reversed by reflushing water through the device. Iodine gas or soluble iodine has the same effect.

Polymerized films may be derivatized prior to transfer or post transfer to the electrode substrate. Chemically reactive groups present on the polymer surface may be modified depending upon their functionality. For example, polymer films with free hydrazine containing polar head groups may be derivatized with aldehyde containing ligands (e.g., periodate cleaved oligosaccharide moieties on antibodies). An advantage to post polymerization processing is that large bulky analyte binding members may be attached to preformed high quality films where as attachment of such groups prior to film formation may interfere with the formation of quality films.

The addition of chemical dopant reagents, such as iodine, significantly enhances the base line conductivity of the sensor. Dopants may be added to the polymer from the gaseous e.g., ion implantation (U.S. Pat. No. 4,647,403) or liquid state. Doping may be permanent (through covalent modification) or reversible.

Post-polymerization treatment of the polymer with a solution of protein such as bovine serum albumin is useful for the purpose of blocking any nonspecific binding sites which may otherwise serve to bind analyte molecules nonspecifically and hence deplete analyte from the solution. In addition, blocking may be useful for reducing nonspecific binding of other cross-reactive materials in the sample which may cause undesirable erroneous results.

Bioelectronic Sensor Applications

The bioelectronic sensor probe design includes a generalized surface for attaching any antibody, ligand binding proteins, organic receptors, or single stranded oligonucleotides. The bioelectronic sensor can, in principle, be used to detect a variety of analytes including viruses, bacteria, parasites, normal and malignant cells, bio-polymers, and small molecules. The sensor approach has direct application in food processing, food quality control, environmental, agricultural, military, medical, veterinary, and other contexts.

Crystalline arrays of strept/avidin bound to polymer surfaces may be utilized for a range of applications other than analyte detection. The high degree of stability provided for by the polymer matrix can, for example, be used for improving the quality of large crystalline protein domains for electron crystallographic analysis. The availability of two free biotin binding sites on each polymer-bound strept/avidin molecule allows a number of relevant molecules to be ordered epitaxially on the crystalline protein surface which ordinarily would not condense into crystalline arrays. The polymer-bound strept/avidin thus provides a template for ordering other biologically, electronically, or structurally important molecules. Crystalline arrays of strept/avidin on crystalline polymer surfaces are useful for circular dichroism measurements. Lattice orientation of the analyte molecule coupled with a net increase in film thickness gives rise to distinct shifts in the circular dichroic spectrum.

Analytes are detected, depending on the particular protocol, by binding to a ligand attached to one of the binding pair members, biotin or strept/avidin. Binding results in an electrical, optical, or structural modulation of the polymerized film. Methods, in addition to those previously described for signal generation in application Ser. No. 366,651, filed Jun. 15, 1989, now U.S. Pat. No. 5,156,810, when coupled with the (strept/avidin)/biotin binding, are useful for bioelectronic sensor transduction.

The electrical measurements described here are performed by a two point electrical contact procedure. Two point measurements require only a film resistance recording between two electrodes. Four point measurements are useful for recording the intrinsic conductivity of the film. Measurements are accomplished by arranging four parallel electrodes.

Competitive immunoassays may be accomplished through the use of antibody-luciferase conjugates. Upon enzyme substrate reaction, light energy is emitted. The emitted light interacts with the polymer through photocharge injection and results in an increase in the conductivity of the polymer film.

A device utilizing optical filtration may be employed. Photocharge injection from the back side of the bioelectronic sensor where the back side has a deposited filter layer provides for a disposable device which is wave length specific.

The advantage of using transparent substrates is that various wave lengths of light may be passed through the filter and substrate so that exposure of the polymerized surfactant can be accomplished efficiently and at a selected wave length. Where the laminated bioelectronic sensor is comprised of an optically transparent substrate, light may be injected from either side of the device.

On-line optical monitoring may be possible by observing birefringent colorimetric changes in transmitted light. On-line sensor applications include biologically sensitive optical polarization for optical detection.

Optical wave guides in combination with layered surfaces and the use of evanescent waves may be useful for optical biosensing where the layered surfaces selectively filter various wave lengths and noise during the optical sensing measurements.

The electrode substrates may be used in various configurations. Individual bioelectronic sensors may be employed, where the surface may have one or a variety of regions, where each of the regions may be exposed to the same or different sample. By virtue of having various electrode arrays, the different regions of the sensor may be independently interrogated for a signal.

Alternatively, combinations of sensors may be used in a variety of ways. Of particular interest is the use of combinations of sensors to provide for flow paths for measuring one or a variety of samples.

Device Configurations

An example of how a flow cell device is built is as follows: two bioelectronic sensors that have been prepared by the method described above and protected by the method described above are laminated face-to-face together with a spacing of approximately 100µ between each surface. The spacing could be as little as 10µ or as great as 3 mm but is more usually about 100µ.

The purpose of the lamination is to provide for a capillary flow cell such that the sample, when injected into one end of the laminated device, is drawn by capillary action through the device so that all of the sample comes in contact with the sensor arrays within the device.

The device provides for a sensor with a configuration optimal for extracting a maximum amount of information about the analyte of interest from a small amount of test fluid in a very efficient manner. The laminated device is practical because it allows the user, performing multiple analyses, to use one droplet of test fluid placed at one end of the capillary flow cell device in a single step.

In order to prevent biologically active material from diffusing from one side of the laminated device to the other side, a thin barrier may be placed between the two sides during manufacturing. The barrier can be a thin sheet of glass, such as a microscope cover slip, or it can be a thin flexible membrane such as teflon, mylar, polyethylene, semipermeable membranes, or the like. The barrier prevents molecules, which may become detached from one sensor surface to diffuse through the solution and reattach to the other sensor surface on the apposing side of the sensor.

If desired, contact between the electrically connecting pads on each bioelectronic sensor is made by a spring loaded connector pad inserted between the two sides of the laminated device. This configuration allows for all of the bioelectronic sensors to be monitored simultaneously. Alternatively, one may interrogate each electrode array separately by having individual leads.

During fabrication of the laminated device, initially the polymer-surfactant film is transferred to the electrode substrate as described above. Then the electrodes are protected with an insulated layer as described above. Finally, protective traces parallel to the electrode substrates are then placed at a thickness several times the thickness of the insulating traces placed over the electrode. This configuration provides for the spacing between the two apposing bioelectronic sensors, so that the active portions of the surface do not come in contact with each other at any point, particularly at the protective traces above the electrodes.

An advantage of using the laminated capillary flow cell device is that sensor signals may be obtained by humidifying the sensor surface and allowing a gaseous analyte to diffuse into the humidified bioelectronic sensor chamber. This configuration will allow for the detection of airborne or gaseous state analytes through their absorption into the humidified layer or the thin aqueous layer that covers the surface of the sensor.

Applications of a device which employs a very thin aqueous layer over the sensor surface as opposed to a deep water reservoir over the sensor include the rapid detection of airborne pathogens, such as virus and bacteria, and the detection of molecules, such as drugs, toxins, carcinogens, or the like.

A technical advantage of using a very thin aqueous absorption layer over the sensor surface as opposed to a deep aqueous reservoir is the rapid diffusion rate of the analyte of interest through the thin layer versus a deep reservoir. In the deep reservoir configuration, mixing or turbulent flow is necessary to ensure that a sufficient amount of analyte comes in contact with the sensor surface. With the thin absorption layer configuration, the analyte can be concentrated to a much higher degree and rapid diffusion through the thin layer ensures quicker, more rapid contact of the analyte with the sensor surface over the thick aqueous layer configuration.

Another advantage of using the laminated flow cell device is that when the substrate is transparent, such as clear plastic or glass, then illumination can occur from either side of the device. In addition, illumination is useful for the purpose of inspection, quality control, and quality assurance during manufacturing of the laminated flow cell device. Illumination of the film can also be used to increase the baseline conductivity of the film several orders of magnitude so that the sensor can respond with more sensitivity to the analyte of interest. Photoelectrical doping increases the sensor signal to noise ratio by bringing the baseline conductivity to a more easily measurable range.

The laminated device can be exposed by intense light for the purpose of measuring photoconductivity from either side. The advantage of having clear substrates for the bioelectronic sensor is that light can be directed through the transparent substrate directly to the polymer film. Because light can be pulsed onto the biolectric sensor from both sides where the sensor is laminated, the intensity of the photoresponse can be made significantly greater than if the light is only directed from one side of the sensor. The end result is that the photoresponse will be significantly higher than if light were directed from only one side of the sensor.

The laminated configuration also provides for symmetrical responsiveness of films which are placed onto apposing sensors. In this configuration the intensity of light directed from either side of the laminated chip can be regulated such that the photoresponses from either device, no matter what the film composition is, can be normalized.

With a single device, by placing and protecting the electrodes in a square or rectangular array, the configuration provides for an efficient sample delivery system. The electrode configuration allows water to be placed over the protected electrode in such a way that the protectant creates a barrier which retains the water. A convenient electrode array size for performing biological measurement is approximately 0.5 $cm^2$. The size should allow for retention of the aqueous droplet above the electrode array. The single device can be converted to a flow cell device with the use of silicon rubber barriers and an attached cover slip to create a flow chamber. In this configuration the silicon rubber acts as a septum such that fine hosing or needles can be used as entrance and exit ports.

The use of interdigitating electrode arrays provides for the convenience of condensing the electrode arrays within a small area. A disadvantage of using long parallel electrode arrays is that the aqueous layer above the electrode must extend over a long distance.

On a typical bioelectronic sensor, ten interdigitating electrode arrays can be placed conveniently in two parallel rows, each having five electrode arrays. This configuration allows for ten independent measurements to be made simultaneously on a single device. These measurements can either be analyzed individually or summed over the entire number of electrode arrays. Interdigitating electrode arrays allow for more of the electrode chip surface area to be exploited by regions useful for detection.

A key advantage to the use of interdigitating electrode arrays is that the ratio of the path length to the distance between the electrodes is very high. The greater the interdigitation and the closer the electrodes, the greater the ratio.

An advantage to reducing the distance between two electrodes is that the ratio of the sensor signal to noise can be significantly enhanced when the ratio of the length to the width between each electrodes is increased. Another advantage to reducing the distance between two electrodes and subsequently increasing the ratio of the length to width between two electrodes is that the total surface area between two electrodes may be minimized. Therefore, less analyte is required to bind to the total surface area between two electrodes. An additional advantage to moving the electrodes closer together is that the parallel versus series resistor effect in the film is increased.

Two-Dimensional Crystallization of Strept/avidin

Two-dimensional crystalline arrays of strept/avidin are formed on the surface films containing 5 mole % of biotinaminocaproylethylenediamino- 10,12-pentacosadiynamide and 5 mole % EA-PDA either in a polymerized or non-polymerized state. Prepolymerization of the films significantly enhances the transfer of strept/avidin crystals to solid supports and eliminates the need to expose biologically active protein to intense ultraviolet light.

Prepolymerized films containing Biotin-CAP-EDA-PDA for strept/avidin crystallization are formed using the method described above. For viewing by electron microscopy, high quality crystalline films are transferred to carbon coated electron microscope grids by placing a grid directly onto the polymer film and carefully lifting the grid vertically. The polymer-coated grids are washed three times with high purity water, allowed to air dry, and then each applied to the surface of 15 microliters of a buffered strept/avidin solution (0.1 mg protein per ml, 10 mM Tris buffer, pH 7.0, 120 mM sodium chloride at 50° C.).

Upon incubation (15 minutes), the grids are removed, washed with high purity water, and stained with uranyl acetate (1.0%). Extensive two-dimensional crystalline arrays are observed by high dose electron microscopy (Philips 201). No crystalline arrays are present on films lacking biotin-aminocaproylethylenediamino-10,12-pentacosadiynamide (Biotin-CAP-EDA-PDA). Similarly, crystalline arrays of strept/avidin are formed on the surface of biotinylated polymer films which have been transferred to electrode substrates. The crystalline arrays are observed by microscopy by the addition of fluoresceinated biotin molecules bound to the available sites on the strept/avidin molecules.

Bioelectronic Sensor Photoconductivity

The photoconductivity sensors prepared with films containing 2.5 mole percentage biotin-CAP-EDA-PDA and 97.5 mole percentage EA-PDA were measured for the purpose of determining the intrinsic film quality. Photoconductivity is used as a measure of sensor performance. The greater the photoelectric response, the greater the sensor performance. Bioelectronic sensors which show significantly high photoelectrical conductivities above background when exposed to a white light source are correlated with high responses upon analyte binding. While not wanting to be tied to any particular theory, it appears that the photoelectronic response of the sensor can be used as a direct correlation with the response of analyte binding.

Bioelectronic sensors prepared with biotinylated films have photoelectrical responses several orders of magnitude above background. A sensor is prepared with silver electrodes by a photolithographic procedure described before (U.S. application Ser. No. 366,651, filed Jun. 15, 1989, now U.S. Pat. No. 5,156,810). The area of the sensor is approximately 0.5 cm$^2$. The electrodes are interdigitating with a ratio of length to width between the electrodes of approximately 60. Ten parallel electrode pairs of these dimensions are spaced such that 10 independent measurements can be performed on a single sensor substrate. The electrode substrate is made hydrophobic for film transfer by alkylation with dimethyloctadecylchlorosilane (DMOCS). Initially, the substrate is cleaned three times in high purity chloroform, drained, rinsed in high purity water, and dried. Film formation, polymerization and transfer is accomplished as described above.

Photoelectric responses are measured with an electrometer (Keithly 614) using settings adjusted to a range setting of $1.0 \times 10^{-8}$ amphere. The electrometer is calibrated with the zero check switch. The sensitivity is adjusted to an appropriate setting (usually setting 2). The baseline current of the bioelectronic sensor device is 4.0–6.0 picoamperes. Pulses of intense light (50–100 ft. candles) are directed to the device surface at a distance of 3 inches. Pulsing results in a current of $4.0 \times 10^{-8}$ to $6.0 \times 10^{-8}$ amperes after 10 sec. exposure.

For further understanding of the invention, the drawings will now be considered.

In FIG. 1, a bioelectronic sensor 12 is shown having an inert substrate 10. On the inert substrate 12 are positioned ten interdigitating arrays 14 of conducting electrodes 16. One set of conducting electrodes 16 is collectively connected to a common lead 20 which is connected to external lead 22 while the other set of interdigitating electrodes 16 is collectively connected to a common lead 24 which is connected to external lead 26. Electrodes 16 are separated by a space 18.

The opposing faces of the bioelectronic sensor may be modified by providing a reflecting surface, or the surfaces may provide for absorption or transmission of specific wave length ranges employing various means, e.g., grating or dye, or one could provide for a dissimilar specific binding pair member with each of the electrode arrays, so that each surface can be used with the same or different analyte.

Figure 2:
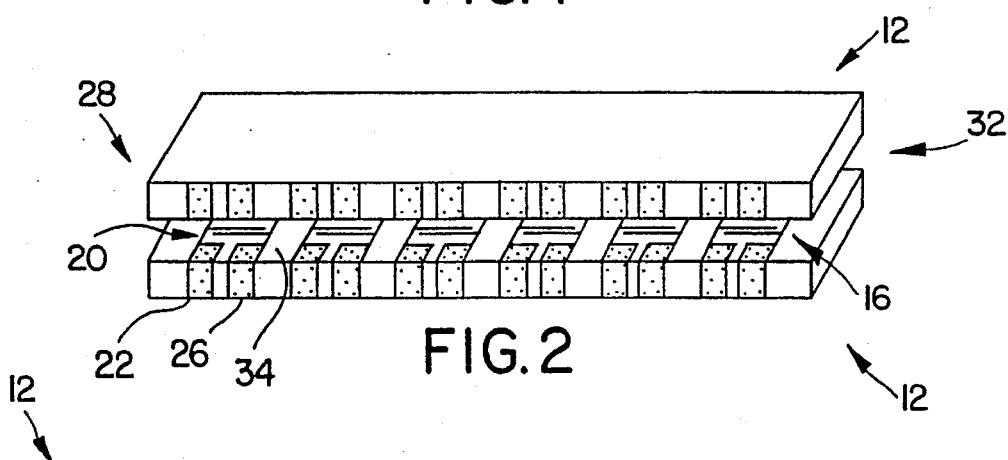
FIG. 2 is a perspective view of two bioelectronic sensor devices joined together.

In FIG. 2, channel device 28 is depicted where two bioelectronic sensors 12 are employed in a confronting relationship. The two bioelectronic sensors 12 define a plurality of channels 32 separated by separation strips 34. New channels may be individually separated by the separation strips being in physical contact or by providing for an inert impervious film which separates the upper channels from the lower channels, as well as providing for a barrier to mixing between the channels 32.

Figure 3:
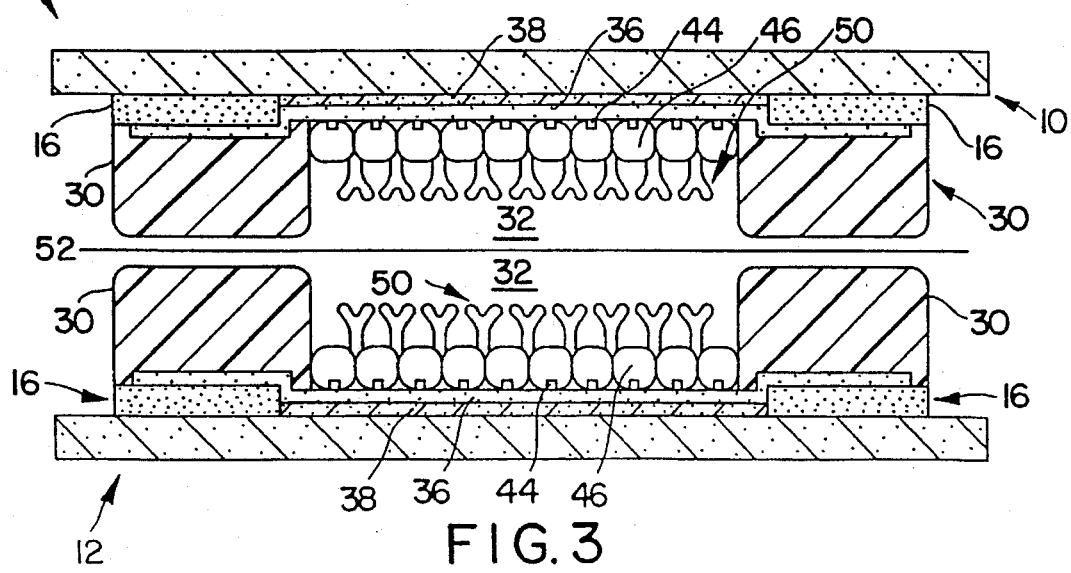
FIG. 3 is a diagrammatic cross-sectional elevational view of the sensor.

In FIG. 3 is depicted a diagrammatic view of a channel device. Electrode 16 on substrate 10 is electrically connected to common leads, not shown. The electrode 16 and organic electrically variably conducting film 36 define an electrical system for responding to changes in the environment. The film 36 is bound to the substrate 10 through an alkylation layer 38 and is in electrical contact with electrodes 16 so that changes in electrical characteristics of the film 36 are readily detected by an external circuit. Electrodes 16 are coated with an electrically inert sealant layer 30 which prevents contact between the electrodes 16 and any aqueous medium in the channel 32. The film 36 is comprised of molecules which have a head ligand 44 which may serve as a specific binding member for binding to a receptor 46. The receptor 46 may have a plurality of sites for binding to the same or different molecules. As depicted, the receptor 46 provides a dimeric unit which binds to a second receptor 50 which serves to recognize the analyte or other molecule, or a related molecule, which has an epitope cross-reactive with the analyte. An inert screen 52 separates the channel 32 into subchannels, which allows for two separate determinations to be made for each of the bioelectronic sensors 12.

Figure 4:
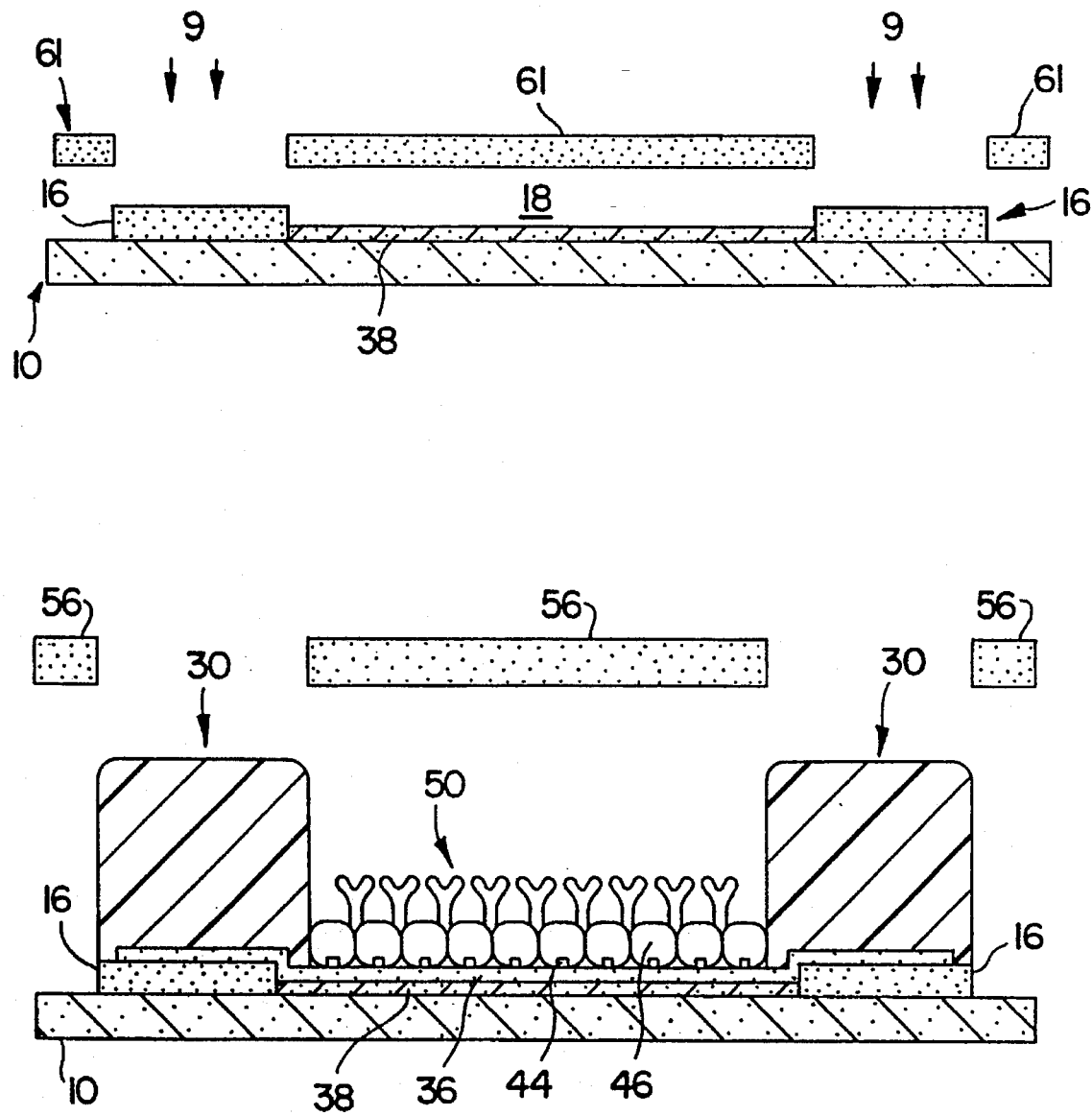
FIG. 4 is a diagrammatic view of assembly of a bioelectronic sensor device.

In FIG. 4 is depicted a schematic view of the device for the preparation of the bioelectronic sensor in accordance with the subject invention. The first step involves the vapor deposition of the metal electrodes onto an insulating surface. Onto substrate 10 which had been pretreated with alkylation layer 38 is vapor deposited metal 9, to form metal electrodes 16, where the sites of deposition are controlled by screen 61. The ultra-thin organic conducting polymer 36, containing the ligand 44, is coated onto the electrodes 16 and the space between the electrodes 16 on the substrate 10. Insulation is then achieved by coating the region over and around the electrodes 16. The sealant material 30, with screen 56, directs the regions which are covered with the sealant 30. The electrically conducting film 36 is then activated with the receptors 46 and 50.

Figure 5:
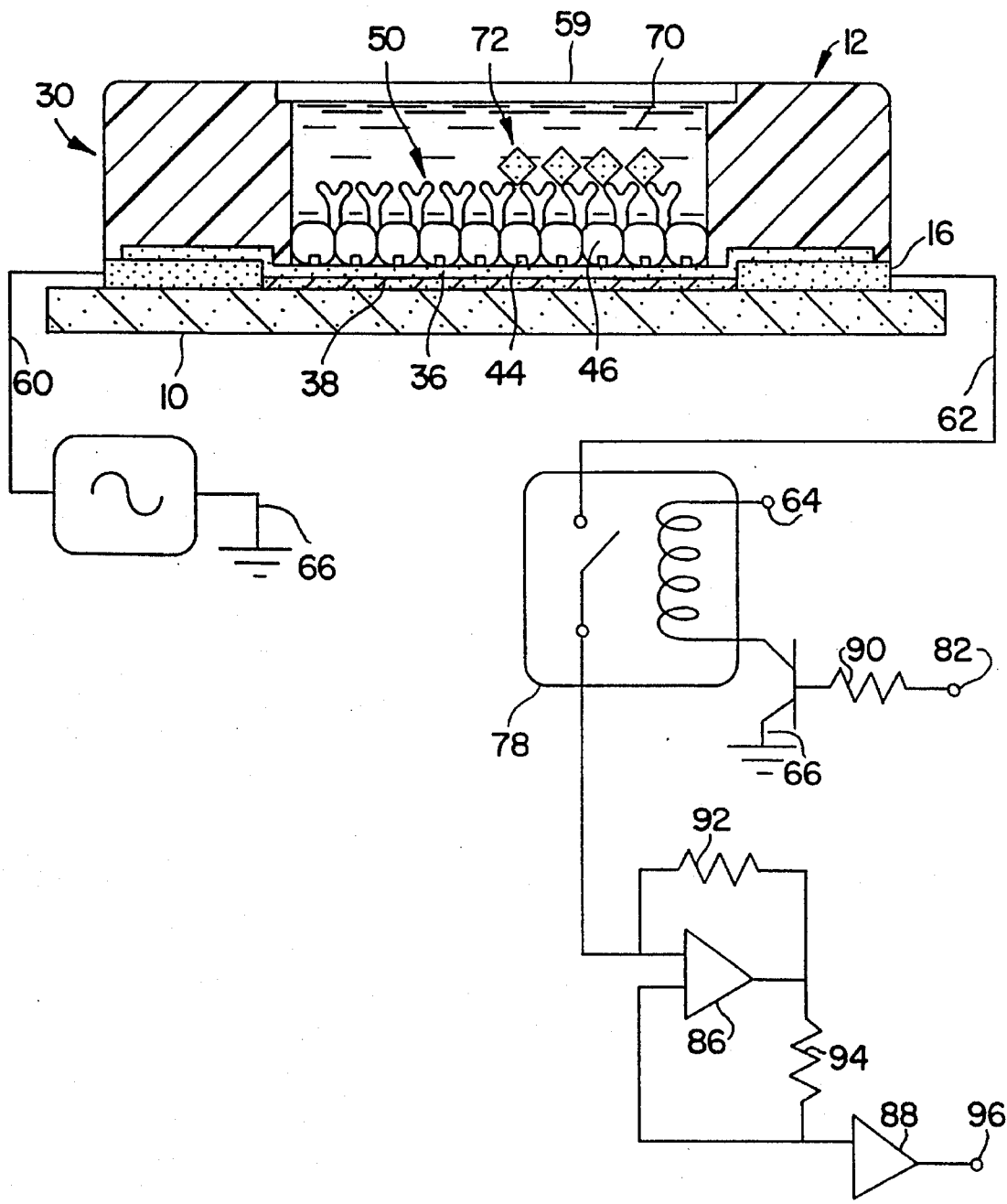
FIG. 5 is a diagrammatic view of a bioelectronic sensor device with an exemplary circuit.

In FIG. 5 is depicted a diagrammatic design of a measurement circuit and bioelectronic sensor. The insulating support 10 supports common electrodes 16 and electrode seal 30 and water barrier 59. To the electrically conducting film 36 is bound receptors 46. Electrodes 16 are connected through external leads, not shown, and through wires 60 and 62 to a source of power 64 and ground 66 for measuring changes in the external signal. Buffer 70 is placed in the area defined by the water barrier 59 and the receptor 50 for receipt of the analyte 72.

When the Hg reed switch 78 closes by a high TTL (transistor-transistor logic) input 82, the voltage source 64 induces a current proportional to the overall impedance of the circuit. Op amp 86 amplifies the current and feeds a log amplifier 88 with the aid of resistors 90, 92, and 94. Voltage output 96 from log amplifier 88 is then inversely proportional to the log of the film resistance.

A second measurement device (not shown) is useful for amplifying differences in bioelectronic sensor output between a positive test sensor and a control sensor. This is accomplished by supplying two bias voltages of opposite polarities to the device, one to a positive test sensor and the other to a control sensor. During a measurement the entire bioelectronic sensor is illuminated with light. The two bias voltages are adjusted such that the sum of the current output, at a summing junction, is zero. The zero output voltage defines a starting baseline for the experiment. During analyte detection only differences between the positive test sensor and the control sensor, caused by specific analyte binding, are electrically amplified above the zero baseline.

The following examples are offered by way of illustration and not by way of limitation.

EXAMPLES

The bioelectronic sensor device was prepared as follows. For various experiments, surfactant-linked ligands were prepared using condensation reactions involving an activated carboxylic acid group and a nucleophilic amine or hydroxyl. 10,12-pentacosadiynoic acid (PDA) was activated with trimethylacetylchloride under anhydrous conditions to form the active asymmetric anhydride. The anhydride was treated with excess ethylene diamine or ethanolamine (in situ) to form ethylenediamino-10,12-pentacosadiynamide (EDA-PDA) or ethanolamine-10,12-pentacosadiynamide (EA-PDA), respectively. 1.5 mole equivalents of diethylamine were added as a catalytic base. Reactions were allowed to proceed for 3 hours at room temperature. EDA-PDA or EA-PDA were chromatographically purified using a silica gel column and a chloroform/methanol gradient. EDA-PDA or EA-PDA were condensed with free carboxylic acid containing ligands (chemically activated as above) to form the ligand-linked polymerizable surfactants. Representative examples of ligand linked surfactants which were prepared by this method for the purpose of fabricating bioelectronic sensors include: 2,4-dinitrophenyl-aminocaproyl-EDA-PDA; theophylline-8-butyryl-EDA-PDA; α-galactose-1,4-β-galactosediethyleneoxide-aminosuccinyl-EDA-PDA; biotin-aminocaproyl-EDA-PDA (Biotin-CAP-EDA-PDA); N-dimethylrifampicin-succinyl-EDA-PDA; dATP-EDA-PDA; and mannose-C-glucosyltetraethyleneoxideamino-10,12-pentacosadiynamide (by —C— is intended a C rather than an O bridge).

2,4-dinitrophenyl-aminocaproyl-EDA-PDA was prepared for fabricating a bioelectronic sensor specific for anti-dinitrophenyl antibodies. Theophylline-8-butyryl-EDA-PDA was prepared for fabricating a bioelectronic sensor specific for antitheophylline antibodies and theophylline assays. Biotin-CAP-EDA-PDA was prepared for the purpose of fabricating bioelectronic sensors which utilize strept/avidin as a binding member for various assays. N-demethylrifampicin-succinyl-EDA-PDA was prepared for the purpose of fabricating a bioelectronic sensor to detect RNA polymerase. dATP-EDA-PDA was prepared for the purpose of fabricating bioelectronic sensors to detect enzymes and other proteins which bind to dATP. α-galactose-1,4,-β-galactose-diethyleneoxide-aminosuccinyl-EDA-PDA was prepared for the purpose of fabricating bioelectronic sensors to detect P. fimbriae strains of E. coli. Mannose-C-glycosyltetraethyleneoxideamino-10,12-pentacosadiyneamide was prepared for the purpose of measuring the mannose positive pili strains of E. coli.

Carbon linked glycosides (C glycosyl at the reducing end of the sugar) are selected on the basis of bond stability, improved binding characteristics to adhesion proteins, and the versatility of chemistry employed.

EA-PDA was also prepared for the purpose of forming mixed polymerized films. Films were usually prepared with 1–10% EA-PDA and 90–99% of any ligand-linked surfactant.

One assay involved dinitrophenyl bound to the surfactant for detection of antibody to dinitrophenyl. The bioelectronic sensor was prepared in the following manner. A glass microscope cover slip (22 mm×22 mm) was alkylated by dipping it into a solution of 5% dimethylchlorosilane and 95% hexane for 5 minutes at room temperature. The cover slip was washed two times with clean chloroform and then rinsed three times with double glass distilled water. The cover slip was air dried and then dusted with a stream of clean dry nitrogen gas.

A polymerized monolayer, containing 2,4-dinitrophenyl (DNP) as the antigen, was prepared and transferred to the alkylated cover slip as follows. A glass microscope slide (precleaned and then dusted with a stream of nitrogen) was placed on a copper plate (10 cm×10 cm square and 0.4 cm thick). 2.0 ml double glass distilled water was applied to one end of the glass slide. 2.0 μl of a solution containing 1.0 mg/ml of monomers (2.5 mole % 2,4-dinitrophenaminocaproylethylenediamine-10,12-pentacosadiynamide and 97.5 mole % ethanolamino-10,12-pentacosadiynamide) were applied to the aqueous surface from a 5 μl micropipette at room temperature in two equal aliquots. Upon evaporation of the solvent, the monomer dried into small visible islands at the water surface. The copper plate was transferred to a preheated hot plate (approximately 200° C. on the hot plate surface). The copper plate, microscope slide, and water were heated until the islands of monomer melted and dissolved at the water surface. The copper plate was transferred after 3–5 minutes heating to a prechilled aluminum block embedded in ice. The copper plate, slide and water were allowed to cool to 4° C.

The monolayer was polymerized with a UV 254 nm short wave lamp (4 watts, 200 microwatts power output at 8 inches) at a distance of 2 inches for 4 minutes. The monolayer appeared pink by eye. Transfer of the polymerized film to the alkylated glass cover slip was accomplished by holding the cover slip horizontal with a pair of fine forceps and slowly lowering the cover slip so that the hydrophobic portion of the film (the side facing air) was directly contacted. Seconds after contact was made between the cover slip and the aqueous surface, the cover slip was pulled away and allowed to air dry. The alkylated glass cover slip appeared homogenously pink after the transfer.

Silver electrodes were applied directly to the monolayer coated cover slip by direct extrusion of silver paint onto the pink polymer surface. The silver paint (electronic grade) was applied with the aid of a thin glass micropipette to create two parallel electrodes (each 8 mm in length and 1 mm wide) with a 2 mm gap between the electrodes. The final surface area between the electrodes was 16 $mm^2$. Adhesive copper strips were contacted to the electrodes. Electrical contact between the electrodes and the copper strips was ensured by applying a small coating of silver paint. The silver paint was allowed to air dry at room temperature for 30 minutes.

The electrodes were electrically insulated from water using a thin paraffin coating (Parafilm). A strip of Parafilm (1.4 cm×2.0 mm) was placed over each electrode to create a channel between the electrodes and so that there were no visible signs of silver paint exposed to air within the channel. The Parafilm strips were carefully pressed on the electrodes using a thin cylindrical glass rod (4.0 mm in dia.). The Parafilm was melted onto the surface of the electrodes and polymer by placing the device into an oven (125° C.) for 2 minutes. After cooling the device to room temperature, the solidified Parafilm formed a water tight barrier over the electrodes.

The bioelectronic sensor device was tested by attaching one copper test lead to the positive terminal of a 10 volt DC power supply and the other to one of three input leads on an electrometer (Kelthly 640). The circuit was completed by connecting other electrometer input leads to power supply, ground and negative voltage terminals. The electrometer output (negative 1.0 volts to positive 1.0 volts) was connected to an A/D converter board which was interfaced with a desk top computer. Electrometer outputs were digitized, converted to actual units of amperes, as measured by the electrometer, and displayed on a color graphics display screen.

Prior to performing a bioelectronic sensor assay, the electrometer settings were adjusted to a range setting of $1.0 \times 10^{-8}$ ampere. The electrometer was calibrated with a zero check switch. The sensitivity was placed to setting 2. The base line current of the bioelectronic sensor device was 4.0 picoamps. The electrical conductivity of the device was inspected by flashing pulses of intense visible light on the polymer surface at a distance of 3 inches.

Buffer was placed on the bioelectronic sensor (tris pH 7.0 with 140 mM NaCl). The assay procedure involved placing 100 ml of buffer on the bioelectronic sensor between the electrodes and within the channel. The reliability of the sensor was tested by flashing pulses of intense visible light at 1 inch distance from the sensor surface. Each light pulse gave a 100-fold increase in current above background. Once the integrity of the film was established, antitdinitrophenyl antibodies (one ml of a one mg/ml solution of antibody) were microinjected into the buffered solution under low room light conditions. Initially a flat base line of 4.0 picoamps was observed. The base line remained stable for several seconds and then a distinct immediate rise in the current to 9.0 picoamps was recorded.

A second assay involved theophylline bound to the surfactant for the detection of an antibody to theophylline.

The bioelectronic sensor employed was prepared in a different manner from the one used in the first assay. Electrode designs are generated using computer aided design and transferred to acetate masks. The masters were used to form chromium-tungsten-silver electrode designs on highly resistive, ultra flat 0.040 inch thick low expansion glass (Corning 7059) and standard lift off photoresist methods.

The electrode-glass substrates, with their approximately 500Å thick electrodes at 0.5 mm spacing in an interdigitating comb pattern, were dipped for two minutes in 5% by weight octadecyldimethylchlorosilane in hexane. The substrates were immediately rinsed by dipping in two successive 1:1 chloroform:methanol baths, followed by immersion for 1 min. in a chloroform bath. The substrates were air dried and left in 18 megaOhm water for 5 min. Drying was carried out under nitrogen gas at 120° C. for 15 min.

The silanized electrode-substrates were then jig-mounted 0.125 inches from the end and square to the edges of a standard 1×3 inch microscope slide to allow registration of the electrode-substrate in all subsequent processes.

Transfer of the freshly polymerized monolayers prepared as above using 2.5 mole % theophylline-8-butyryl-EDA-PDA and 95 mole % EA-PDA was accomplished manually by inverting the chip and moving it downward to contact the monolayer at a 5 degree to 15 degree angle to the surface. When the entire electrode surface had made contact, the chip was lifted free from the surface in a slight rocking motion to pull the monolayer from the surface and meniscus-strip excess subphase liquid from the chip. The completed chips were jig-rinsed with 150 ml of 18 megaOhm water, then dried in a nitrogen atmosphere at 100° C. for 5 to 15 min.

Electrode-substrates were stored in a slide box under dry nitrogen gas until tested. Each cell of the chip was tested for photoresponse. Film containing electrode-substrates were numbered and the photoresponse data stored for future use if the photoresponses signal above background was in the range of 1 100 to 10,000 fold increase.

To prepare electrode-substrates for biological testing, a thin bead of black silicone rubber resin as protectant was traced over the monolayer following the pattern and extending slightly beyond the dimensions of the metallic conductors. The silicon rubber protective traces were made as described above to a resolution of 200 microns. Finally, a larger boundary of silicone rubber was applied in a pattern to isolate individual cells and define the flow-cell boundaries. A thin glass cover slip was then applied to the partially cured silicone traces to complete the flow cell.

50 µl of buffer (10 mM tris pH 7.0, 120 mM NaCl) were placed over the sensor. Photoresponses were monitored as above in the presence of buffer. The responses were of a similar increase as before. Once the integrity of the film was established, antitheophylline antibodies (10 µl of one mg protein/ml solution) were microinjected into the buffered solution while maintaining low ambient light. Initially a flat base line of 3.0 picoamps was observed. The base line remained stable for several seconds and then a distinct immediate rise in the current to 8.0 picoamps was recorded within 2 minutes. Photoresponses were taken again with a distinct decrease (20%) in the resulting photocurrent. The new base line remained stable for 30 more minutes at which time the assay was terminated.

A third assay involved biotin bound to the surfactant for the detection of avidin. 50 µl of buffer (same as above) were placed over the sensor. Photoresponses were monitored as before. Current increases from picoamps to nanoamps were recorded. Once the integrity of the film was established, avidin (one µl of one mg protein/ml solution) was microinjected into the buffered solution. Initially a flat base line of picoamps was observed. The base line remained stable for several seconds and then a distinct immediate 3-fold rise in the current above background was recorded within one minute. The photoresponsiveness of the film showed a significant decrease in current upon avidin binding (15%). The new base line remained stable for 30 more min. at which time the assay was terminated.

A fourth assay involved the use of fluorescence measurements for the detection of antitheophylline antibodies on a sensor with theophylline bound to the polymer film. The sensor was placed under a fluorescence microscope objective such that the polymer film could be viewed at 75 times magnification using a rhodamine filter. 500 μl of a buffer solution was placed on the film so that the microscope objective was immersed in the buffer. The film appeared dull orange in color and intensity. 20 μl of a 1.0 mg/ml solution of antitheophylline antibodies were microinjected into the buffer. Immediately upon injection, the intensity of fluorescence increased by 75%. The intensity of a control film which contained no theophylline was unaffected by the antitheophylline antibody.

It is evident from the above results, that a sensitive technique is provided for the detection of a wide range of analytes. Numerous different techniques may be employed for detecting an electrical or light signal associated with a change in the properties of a surfactant polyunsaturated polymer. By employing different protocols, the analytes of interest may range from haptens and antigens, to aggregations, such as viruses, cells, or the like. By employing different detection methods such as optical circular dichroism, measurements may be taken with a variety of different instrumentation.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for detecting the presence of an analyte in a sample, wherein said analyte is a ligand or a receptor of a specific binding pair, said method comprising:

contacting said sample with a polymerized surfactant layer having optical properties, polymerized from polyunsaturated surfactant monomers of the formula:

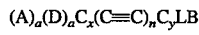

$$(A)_a(D)_a C_x(C\equiv C)_n C_y LB$$

wherein:
A is a functionality for linking to an underlying substrate;
a is 0 or 1;
C is carbon:
x and y are at least 1 and the sum of x and y is in the range of 4–32;
n is 2;
D and L are bond or linking groups; and
B is a specific binding member which binds to said receptor;

with one terminus of each of said monomers proximal to the underlying substrate and the other terminus comprising B, said polymerization occurring at the C≡C groups of said monomers;

wherein said optical properties of said surfactant layer change due to specific binding of said receptor to B, with the proviso that when said analyte is said ligand aid sample comprises a predetermined amount of said receptor;

detecting said change in said optical properties upon specific binding of said receptor to B; and relating said change to the presence of said analyte in said sample;

whereby the presence of said analyte in said sample is detected.

2. The method according to claim 1, wherein said change in said optical properties of said surfactant layer is a change in absorbance properties of said surfactant layer.

3. The method according to claim 1, wherein said change in said optical properties of said surfactant layer is a change in fluorescence emission properties of said surfactant layer.

4. A method for detecting the presence of an analyte in a sample, wherein said analyte is a ligand or a receptor of a specific binding pair, said method comprising:

contacting said sample with a polymerized surfactant layer, polymerized from polyunsaturated surfactant monomers of the formula:

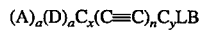

$$(A)_a(D)_a C_x(C\equiv C)_n C_y LB$$

wherein:
A is a functionality for linking to an underlying substrate;
a is 0 or 1;
C is carbon:
x and y are at least 1 and the sum of x and y is in the range of 4–32;
n is 2;
D and L are bond or linking groups; and
B is a specific binding member which binds to said receptor;

with one terminus of each of said monomers proximal to the underlying substrate and the other terminus comprising B, said polymerization occurring at the C≡C groups of said monomers;

wherein absorbance properties of said surfactant layer change in response to conformational changes of said surfactant layer due to specific binding of said receptor to B, with the proviso that when said analyte is said ligand said sample comprises a predetermined amount of said receptor;

comparing said absorbance properties between said sample-contacted surfactant layer with absorbance properties of a control; and relating any difference in absorbance properties between said sample-contacted surfactant layer and said control to the presence of said analyte in said sample;

whereby the presence of said analyte in said sample is detected.

5. A method for detecting the presence of an analyte in a sample, wherein said analyte is a ligand or a receptor of a specific binding pair, said method comprising:

contacting said sample with a polymerized surfactant layer, polymerized from polyunsaturated surfactant monomers of the formula:

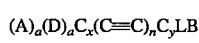

$$(A)_a(D)_a C_x(C\equiv C)_n C_y LB$$

wherein:

A is a functionality for linking to an underlying substrate;

a is 0 or 1;

C is carbon:

x and y are at least 1 and the sum of x and y is in the range of 4–32;

n is 2;

D and L are bond or linking groups; and

B is a specific binding member which binds to said receptor;

with one terminus of each of said monomers proximal to the underlying substrate and the other terminus comprising B, said polymerization occurring at the C≡C groups of said monomers;

wherein fluorescence emission properties of said surfactant layer change due to specific binding of said receptor to B, with the proviso that when said analyte is said ligand said sample comprises a predetermined amount of said receptor;

comparing said fluorescence emission properties between said sample-contacted surfactant layer with fluorescent emission properties of a control; and relating any difference in fluorescence emission properties between said sample-contacted surfactant layer and said control to the presence of said analyte in said sample;

whereby the presence of said analyte in said sample is detected.

* * * * *